US007368434B2

(12) United States Patent
Keung et al.

(10) Patent No.: US 7,368,434 B2
(45) Date of Patent: May 6, 2008

(54) COMPOUNDS USEFUL FOR THE INHIBITION OF ALDH

(75) Inventors: Wing Ming Keung, Wayland, MA (US); Bert L. Vallee, Boston, MA (US); Guangyao Gao, Knoxville, TN (US)

(73) Assignee: The Endowment for Research in Human Biology, Inc., Cambridge, MA (US)

(*) Notice: Subject to any disclaimer, the term of this patent is extended or adjusted under 35 U.S.C. 154(b) by 497 days.

(21) Appl. No.: 10/609,120

(22) Filed: Jun. 27, 2003

(65) Prior Publication Data

US 2004/0068003 A1 Apr. 8, 2004

Related U.S. Application Data

(60) Provisional application No. 60/391,907, filed on Jun. 27, 2002.

(51) Int. Cl.
*A61K 31/20* (2006.01)

(52) U.S. Cl. ........................ 514/27; 514/456; 549/402; 549/403

(58) Field of Classification Search ................ 549/403, 549/402; 514/27, 456
See application file for complete search history.

(56) References Cited

U.S. PATENT DOCUMENTS

| | | | | |
|---|---|---|---|---|
| 3,907,830 A * | 9/1975 | Feuer et al. | 549/403 |
| 4,166,862 A * | 9/1979 | Feuer et al. | 514/456 |
| 4,960,908 A * | 10/1990 | Ito et al. | 549/403 |
| 5,204,369 A | 4/1993 | Vallee et al. | 514/456 |
| 5,624,910 A | 4/1997 | Vallee et al. | 514/27 |
| 5,679,806 A * | 10/1997 | Zheng et al. | 549/403 |
| 5,783,189 A * | 7/1998 | Pei et al. | 514/23 |
| 5,885,028 A | 3/1999 | Blanchard et al. | 405/210 |
| 5,886,028 A * | 3/1999 | Vallee et al. | 514/456 |
| 6,121,010 A | 9/2000 | Vallee et al. | 435/26 |
| 6,255,497 B1 | 7/2001 | Vallee et al. | 549/403 |

FOREIGN PATENT DOCUMENTS

| | | |
|---|---|---|
| FR | 2190411 | * 6/1972 |
| WO | WO 91/15483 | 10/1991 |

OTHER PUBLICATIONS

Jagdish et al., J. Liq. Chrom., 3(7), pp. 1095-1104, 1980.*

Shao, GX et al 'Studies on the synthesis and structure-antihypoxia activity relations of daidzein, an active principle of Pueraria pseudohiruta, and its derivatives' CA 94:174809 (1981).*

Lei, Y et al 'Synthesis and preliminary studies on bioactivities of 7-hydroxy-4'-methylisoflavone' CA 137:185330 (2001).*

Tseng, T et al 'Synthesis of daidzein derivatives' CA 104:206988 (1986).*

Zhou, G et al 'Preparation and bioactivities of formononetin derivatives' CA 134:266171 (2000).*

Diedrich, D Preparation and physical properties of some desoxybenzoins and isoflavones, J. Chem. & Engineering Data, 22(4), 1977, 448-451.*

Baker and Robinson, "Synthetical Experiments in the *iso*Flavone Group. Part III. A Synthesis of Genistein," *J. Chem. Soc.* pp. 3115-3118 (1928).

Baker et al., "*A new synthesis of isoflavones,*" Part II. *J. Chem. Soc.*, pp. 1860-1864 (1953).

Gao et al., "Synthesis of Potential Antidipsotropic Isoflavones: . . . ," *J. Med. Chem.* 44:3320-3328 (2001).

Gao et al., "Synthesis of Daidzin Analogues as Potential Agents for Alcohol Abuse," *Bioorganic & Medicinal Chemistry,* 11:4069-4081 (2003).

Heyman et al., "Daidzin Decreases Ethanol Consumption in Rats," *Acad. Clin. and Exp. Res.*, 20(6):1083-1087 (1996).

Keung et al., "Daidzin and daidzein suppresses free-choice ethanol intake by Syrian Golden hamsters," *Proc. Natl. Acad. Sci. USA,* 90:10008-10012 (1993).

Keung et al., "Therapeutic lessons from traditional Oriental medicine to contemporary Occidental pharmacology," *EXS* 71:371-381 (1994).

Keung et al., "Daidzin inhibits mitochondrial aldehyde dehydrogenase and suppresses ethanol intake of Syrian golden hamsters," *Proc. National. Acad. Sci. USA,* 94:1675-1679 (1997).

Keung et al., "Daidzin and its antidipsotropic analogs inhibit serotonin and dopamine metabolism in isolated mitochondria," *Proc. Natl. Acad. Sci. USA,* 95:2198-2203 (1998).

Li et al., "Synthesis of isoflavones derivatives (I)-7-methoxy-3'-N, N-dialkylaminomethyl-4'-hydroxy isoflavones," *Chinese J. Med. Chem.*, 1(2):38-42 (1991).

Lin et al., "Isoflavonoid Compounds Extracted from *Pueraria lobata* Suppress Alcohol Preference in a Pharmacogenetic Rat Model of Alcoholism," *Alcohol. Clin. Exp. Res.*, 20:659-663 (1996).

Nilsson and Tottmar, "Biogenic aldehydes in brain: on their preparation and reactions with rat brain tissue," *J. Neurochem.*, 48:1566-1572 (1987).

Rooke et al., "The Mitochondrial Monoamine Oxidase—Aldehyde Dehydrogenase Pathway . . . ", *J. Med. Chem.*, 43:4169-4179 (2000).

Strejan et al., "Suppression of Chronic-Relapsing Experimental Allergic Encephalomyelitis in Strain-13 Guinea Pigs by Administration of Liposome-Associated Myelin Basic Protein," *J. Neuroimmunol.* 7:27-41 (1984).

* cited by examiner

*Primary Examiner*—Janet L. Andres
*Assistant Examiner*—Raymond Covington
(74) *Attorney, Agent, or Firm*—CV Therapeutics, Inc.

(57) ABSTRACT

The present invention provides novel antidipsotropic compounds. The invention further provides methods of inhibiting ALDH-2 using the compounds described herein. Methods for modulating alcohol consumption, alcohol dependence and/or alcohol abuse by administering the compounds of the invention to an individual are also provided. The present invention further provides a rationale for designing additional novel antidipsotropic compounds.

12 Claims, No Drawings

COMPOUNDS USEFUL FOR THE INHIBITION OF ALDH

RELATED APPLICATIONS

This application claims priority to U.S. Provisional Patent Application No. 60/391,907, filed on Jun. 27, 2002, hereby incorporated by reference in its entirety for all purposes.

BACKGROUND OF THE INVENTION

1. Field of the Invention

The present invention relates to compounds and methods for modulating alcohol consumption, alcohol dependence and/or alcohol abuse.

2. Description of the Related Art

Excessive alcohol consumption, alcohol dependence and alcohol abuse are among the most serious drug problems of Western societies. In the United States, it is estimated that up to 10% of the population abuse alcohol. The economic cost to the nation is estimated at more than $185 billion per year. Excessive alcohol consumption also brings with it social and psychological damages such as children born with fetal alcohol syndrome, alcohol related accidents, marital disharmony, spousal or child abuse, and the like. Accordingly, safe and effective treatments for limiting and/or preventing alcohol consumption are needed.

Success in the development of pharmacotherapies for addictive disorders, including nicotine and opioid addiction, and a more widespread recognition that alcohol dependence and abuse is a medical rather than moral problem have harnessed growing support in the search for and development of pharmaceutical agents for this medical condition. However, as alcoholism is a complex disease promoted by a wide range of factors, it has been difficult to develop effective modulators of alcohol consumption.

The compound daidzin has been shown to selectively suppress ethanol intake in ethanol-preferring Syrian golden hamsters as well as in other ethanol-drinking animal models such as rats (Keung et al. (1993) *Proc. Natl. Acad. Sci. USA* 90:10008; Keung et al (1994) *EXS* 71:371; Overstreet et al. (1996) *Alcohol. Clin. Exp. Res.* 20:659; Lin et al. (1996) *Alcohol. Clin. Exp. Res.* 20:1083-1087). However, daidzin administered orally does not affect hamster ethanol intake.

Daidzin inhibits the conversion of monoamines such as serotonin (5-HT) and dopamine (DA) into their respective acid metabolites, 5-hydroxyindole-3-acetic acid (5-HIAA) and 3,4, -dihydrozyphenylacetic acid (DOPAC), in isolated hamster and rat liver mitochondria (Keung et al. (1998) *Proc. Natl. Acad. Sci. USA* 95:2198). Recent data indicates that the antidipsotropic activity of daidzin is not mediated by the monoamines but rather by their respective metabolic aldehyde intermediates, 5-hydroxyindoleacetaldehyde (5-HIAL) and/or 3,4-dihydroxyphenylacetaldehyde (DOPAL), which accumulate in the presence of daidzin.

Several recent patents and a pending patent application address the use of daidzin and daidzin analogs useful for the inhibition of aldehyde dehydrogenase and/or alcohol consumption. U.S. Pat. Nos. 5,204,369, 5,624,910 and 5,885,028 disclose methods of inhibiting the mitochondrial aldehyde dehydrogenase (ALDH-2) or treating alcohol consumption using daidzin and specific daidzin analogs. U.S. Pat. No. 6,121,010 discloses screening assays used to identify compounds for reducing alcohol consumption. U.S. Pat. No. 6,255,497 provides compounds which are daidzin analogs. U.S. Utility application Ser. No. 09/616,718 is directed to methods for inhibiting ALDH-2 and reducing alcohol consumption in a human using daidzin analogs. Each issued patent and patent application is incorporated herein by reference in its entirety.

Despite the development of compounds such as daidzin and daidzin analogs, there remains a need to develop antidipsotropic compounds having improved efficacy and enhanced pharmacological properties.

SUMMARY OF THE INVENTION

Accordingly, the present invention provides novel compounds for inhibiting mitochondrial aldehyde dehydrogenase (ALDH-2). These compounds have antidipsotropic properties and are useful for modulating (i.e., reducing) alcohol consumption, therapeutically treating alcohol dependence (i.e., alcoholism) and/or therapeutically treating alcohol abuse. In one embodiment, the present invention provides methods of synthesizing novel compounds for inhibiting ALDH-2.

Another embodiment of the present invention is directed to methods of inhibiting ALDH-2 activity using the compounds set forth herein. Another embodiment of the present invention is directed to a method of modulating (i.e., reducing or inhibiting) alcohol consumption, alcohol dependence, and/or alcohol abuse in an individual by increasing the concentration of an aldehyde in the individual using the compounds set forth herein. In one embodiment, the aldehyde is formed during the catabolism of a neurotransmitter such as, for example 5-HT or DA. In another embodiment, the aldehyde is 5-HIAL and/or DOPAL. In still another embodiment, alcohol consumption is modulated in a mammal such as a human.

The compounds may be administered to individuals using a variety of routes. In one embodiment, the compounds are administered orally. In another embodiment, the compounds are administered intraperitoneally and/or intramuscularly.

Yet another embodiment of the present invention is directed to identifying a compound that modulates (e.g., inhibits) ALDH-2 activity using the compounds set forth herein by contacting ALDH-2 with the compound and determining the ability of the compound to modulate ALDH-2 activity. In one embodiment, the compound increases the concentration of an aldehyde. In another embodiment, the aldehyde is 5-HIAL and/or DOPAL. In another embodiment, the compound does not inhibit MAO.

Compounds of the present invention are set forth herein below. Compounds of the invention may have an OH or an $NH_2$ moiety at the $R_5$ position. Certain compounds of the invention may have a straight chain alkyl at the $R_1$ position.

Combinations of features and methods described herein are also provided.

DETAILED DESCRIPTION OF THE INVENTION

The present invention pertains to compounds of formula I

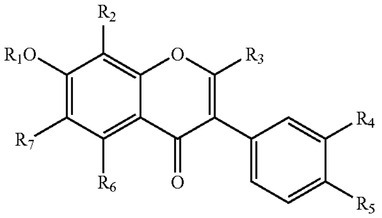

wherein $R_1$ is selected from the group consisting of hydrogen, carboxy, halo, branched or unbranched $(C_1-C_6)$alkyl, $(C_1-C_6)$haloalkyl, $(C_2-C_6)$alkenyl, $(C_3-C_6)$alkadienyl, $(C_1-C_6)$ alkoxy, $(C_3-C_6)$cycloalkoxy, $(C_1-C_6)$haloalkoxy, $(C_3-C_6)$cyclohaloalkoxy, $(C_2-C_6)$alkynyloxy, $(C_1-C_6)$alkoxy$(C_1-C_6)$ alkyl, $(C_3-C_6)$cycloalkoxyalkyl, $(C_1-C_6)$alkoxy$(C_3-C_6)$ cycloalkyl, $(C_1-C_6)$alkylcarbonyl, $(C_3-C_6)$ cycloalkylcarbonyl, $(C_1-C_6)$alkoxycarbonyl, $(C_4-C_6)$ alkoxycarbonylalkyl, $(C_1-C_6)$hydroxyalkyl, substituted or unsubstituted phenyl, phenyl$(C_1-C_6)$alkyl, heterocyclyl, heterocyclyloxy, and heterocyclylcarbonyl, wherein substituents are from one to four and are selected from the group consisting of halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkylamino, di$(C_1-C_3)$alkylamino, $(C_1-C_2)$alkoxy$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$ alkoxycarbonyl, $(C_1-C_3)$alkylaminocarbonyl, and di $(C_1-C_3)$ alkylaminocarbonyl;

$R_2$ is selected from the group consisting of hydrogen, alkoxy, and sugars;

$R_3$ is selected from the group consisting of hydrogen $C_1-C_6$ alkoxycarbonyl, carboxy and sugar;

$R_4$ is selected from the group consisting of hydrogen and hydroxide;

$R_5$ is selected from the group consisting of hydrogen, carboxy, hydroxy, halo, branched or unbranched $(C_1-C_6)$ alkyl, $(C_1-C_6)$haloalkyl, $(C_2-C_6)$alkenyl, $(C_3-C_6)$alkadienyl, $(C_1-C_6)$alkoxy, $(C_3-C_6)$cycloalkoxy, $(C_1-C_6)$haloalkoxy, $(C_3-C_6)$cyclohaloalkoxy, $(C_2-C_6)$alkynyloxy, $(C_1-C_6)$alkoxy $(C_1-C_6)$alkyl, $(C_3-C_6)$cycloalkoxyalkyl, $(C_1-C_6)$alkoxy$(C_3-C_6)$cycloalkyl, $(C_1-C_6)$alkylcarbonyl, $(C_3-C_6)$cycloalkylcarbonyl, $(C_1-C_6)$alkoxycarbonyl, $(C_4-C_6)$ alkoxycarbonylalkyl, $(C_1-C_6)$hydroxyalkyl, substituted or unsubstituted phenyl, phenyl$(C_1-C_6)$alkyl, heterocyclyl, heterocyclyloxy, and heterocyclylcarbonyl, wherein substituents are from one to four and are selected from the group consisting of halo, aminocarbonyl, aminothiocarbonyl, carboxy, formyl, hydroxy, amino, carbamoyl, $(C_1-C_3)$alkyl, $(C_1-C_3)$haloalkyl, $(C_1-C_3)$alkoxy, $(C_1-C_3)$haloalkoxy, $(C_1-C_3)$alkylamino, di$(C_1-C_3)$alkylamino, $(C_1-C_2)$alkoxy$(C_1-C_2)$alkyl, $(C_1-C_2)$alkylamino$(C_1-C_2)$alkyl, di$(C_1-C_2)$alkylamino$(C_1-C_2)$alkyl, $(C_1-C_3)$alkylcarbonyl, $(C_1-C_3)$ alkoxycarbonyl, $(C_1-C_3)$alkylaminocarbonyl, and di $(C_1-C_3)$ alkylaminocarbonyl;

$R_6$ is selected from the group consisting of hydrogen and hydroxide; and $R_7$ is selected from the group consisting of hydrogen, halogen, and $C_1-C_6$ alkoxy.

Because the compounds of formula I above may contain a number of optically active carbon atoms, they may exist as enantiomers, diastereomers, stereoisomers, or their mixtures. The compounds of formula I may optionally exist as tautomers.

As used herein, the term "alkyl" includes both branched and straight chain alkyl groups. Typical alkyl groups include, for example, methyl, ethyl, n-propyl, isopropyl, n-butyl, sec-butyl, isobutyl, tert-butyl, n-pentyl, isopentyl, n-hexyl, n-heptyl, isooctyl, nonyl, decyl and the like.

As used herein, the term "halo" refers to fluoro, chloro, bromo or iodo.

As used herein, the term "haloalkyl" refers to an alkyl group substituted with one or more halo groups such as, for example, chloromethyl, 2-bromoethyl, 3-iodopropyl, trifluoromethyl, perfluoropropyl and the like.

As used herein, the term "hydroxyalkyl", refers to an alkyl group substituted with one or more hydroxy groups such as, for example, hydroxymethyl, 2,3-dihydroxybutyl and the like.

As used herein, the term "alkenyl" refers to an ethylenically unsaturated hydrocarbon group, straight or branched chain, having 1 or 2 ethylenic bonds such as, for example, vinyl, allyl, 1-butenyl, 2-butenyl, isopropenyl, 2-pentenyl and the like.

As used herein, the term "alkylcarbonyl" refers to an alkylketo functionality, for example acetyl, n-butyryl and the like.

As used herein, the term "heterocyclyl" or "heterocycle" refers to a substituted or unsubstituted; saturated, partially unsaturated, or unsaturated 5 or 6-membered ring containing one, two or three heteroatoms, preferably one or two heteroatoms independently selected from oxygen, nitrogen and sulfur. Examples of heterocyclyls include, for example, pyridyl, thienyl, furyl, pyrimidinyl, pyrazinyl, quinolinyl, isoquinolinyl, pyrrolyl, indolyl, tetrahydrofuryl, pyrrolidinyl, piperidinyl, tetrahydropyranyl, morpholinyl, piperazinyl, dioxolanyl, dioxanyl and the like.

As used herein, the term "alkoxy" includes both branched and straight chain alkyl groups attached to a terminal oxygen atom. Typical alkoxy groups include, for example, methoxy, ethoxy, n-propoxy, isopropoxy, tert-butoxy and the like.

As used herein, the term "haloalkoxy" refers to an alkoxy group substituted with one or more halo groups such as, for example chloromethoxy, trifluoromethoxy, difluoromethoxy, perfluoroisobutoxy and the like.

As used herein, the term "alkylthio" includes both branched and straight chain alkyl groups attached to a terminal sulfur atom such as, for example methylthio.

As used herein, the term "haloalkylthio" refers to an alkylthio group substituted with one or more halo groups such as, for example trifluoromethylthio.

As used herein, the term "alkoxyalkyl" refers to an alkyl group substituted with one or more alkoxy groups such as, for example, isopropoxymethyl, or methoxymethoxymethyl.

Prophylactic Methods

In one aspect, the invention provides a method for modulating alcohol consumption and/or preventing alcohol dependence and/or abuse in a subject, by administering to the subject an agent which inhibits ALDH-2 and/or increases aldehyde concentrations (such as 5-hydroxyindoleacetaldehyde and/or 3,4-dihydroxyphenylacetaldehyde). Administration of a prophylactic agent can occur prior to the manifestation of symptoms of diseases or disorders characteristic of alcohol dependence and/or abuse, such that alcohol dependence and/or abuse is prevented or, alternatively, delayed in its progression.

Therapeutic Methods

Another aspect of the invention pertains to methods of modulating (e.g., reducing) alcohol consumption, alcohol dependence and/or alcohol abuse for therapeutic purposes. Accordingly, in an exemplary embodiment, the modulatory method of the invention involves contacting ALDH-2 with a compound that inhibits ALDH-2. In yet another exemplary embodiment, the modulatory method involves administering a compound that increases the concentration of an aldehyde (e.g., 5-HIAL and/or DOPAL) formed during catabolism of a neurotransmitter (e.g., 5-HT and/or DA). Preferably, the compound does not inhibit MAO, or inhibits MAO only to a small degree.

Another embodiment of the present invention involves a method of modulating alcohol consumption for the treatment of alcohol abuse or dependence which includes the step of administering a therapeutically effective amount of a compound which inhibits ALDH-2, and/or increases the concentration of an aldehyde (e.g., 5-HIAL and/or DOPAL) formed during catabolism of a neurotransmitter (e.g., 5-HT and/or DA). As defined herein, a therapeutically effective amount of compound (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of the compound can include a single treatment or, preferably, can include a series of treatments. It will also be appreciated that the effective dosage of in used for treatment may increase or decrease over the course of a particular treatment.

Monitoring of Effects During Clinical Trials

Monitoring the influence of compounds on the modulation of alcohol consumption, dependence and/or abuse can be applied in clinical trials. For example, the effectiveness of an agent determined by a screening assay as described herein to decrease alcohol consumption, dependence and/or abuse, can be monitored in clinical trials of subjects exhibiting alcohol dependence and/or abuse. In such clinical trials, decreased consumption of alcohol can be used as a "read out."

For example, and not by way of limitation, ALDH-2 activity is decreased in cells treated with a compound which inhibits ALDH-2 and as a consequence diverts part of 5-HT metabolic flux from the oxidative pathway, which leads to the formation of 5-hydroxyindoleacetic acid (5-HIAA) to the reductive pathway, further leading to the formation of 5-hydroxytryptophol (5-HTOL). Thus, to study the effect of agents on alcohol dependence and/or abuse, for example, in a clinical trial, urine samples can be collected and levels of 5-HIAA and 5-HTOL in the samples can be determined. Decreased levels of 5-HIAA and increased levels of 5-HTOL will indicate inhibition of ALDH-2 activity. In this way, the urine [5-HTOL]/[5-HIAA] ratio can serve as a marker, indicative of the physiological response of the cells to the compound. Accordingly, this response state may be determined before, and at various points during treatment of the individual with the compound.

In one embodiment, the present invention provides a method for monitoring the effectiveness of treatment of a subject with a compound including the steps of (i) obtaining pre-administration urine samples from a subject before and after alcohol detoxification but prior to administration of the compound; (ii) determining the [5-HTOL]/[5-HIAA] ratios in the pre-administration samples; (iii) obtaining one or more post-administration samples from the subject; (iv) determining the [5-HTOL]/[5-HIAA] ratio in the post-administration samples; (v) comparing the [5-HTOL]/[5-HIAA] ratios in the pre-administration samples with that in the post administration sample or samples; and (vi) altering the administration of the agent to the subject accordingly. For example, increased administration of the compound may be desirable to increase the [5-HTOL]/[5-HIAA] ratio to higher levels than detected, i.e., to increase the effectiveness of the agent. In one embodiment, the ratio of [5-HTOL]/[5-HIAA] in the urine of a detoxified subject is increased back to that of pre-detoxified state. Alternatively, decreased administration of the compound may be desirable to decrease [5-HTOL]/[5-HIAA] ratio to lower levels than detected, i.e., to decrease the effectiveness of the compound. According to such an embodiment, ALDH-2 inactivation and/or an increase in urine [5-HTOL]/[5-HIAA] ratio may be used as an indicator of the effectiveness of a compound, even in the absence of an observable phenotypic response.

Pharmaceutical Compositions

Methods of administering a compound to an individual include providing pharmaceutically acceptable compositions. In one embodiment, pharmaceutically acceptable compositions comprise a therapeutically effective amount of one or more of the compounds described herein, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment, spray or patches applied to the skin; or (4) intravaginally or intrarectally, for example, as a pessary, cream or foam. In another embodiment, the therapeutic compound is administered orally. The compounds of the invention can be formulated as pharmaceutical compositions for administration to a subject, e.g., a mammal, including a human.

The compounds of the invention are administered to subjects in a biologically compatible form suitable for pharmaceutical administration in vivo. By "biologically compatible form suitable for administration in vivo" is meant a compound to be administered in which any toxic effects are outweighed by the therapeutic effects of the compound. The term subject is intended to include living organisms such as mammals. Examples of subjects include humans, monkeys, pigs, dogs, cats, hamsters, rabbits, mice, rats, and transgenic species thereof. Administration of a therapeutically active amount of the therapeutic compositions of the present invention is defined as an amount effective, at dosages and for periods of time necessary to achieve the desired result. For example, a therapeutically active amount of a compound of the invention may vary according to factors such as the disease state, age, sex, and weight of the individual, and the ability of antibody to elicit a desired response in the individual. Dosage regimes may be adjusted to provide the optimum therapeutic response. For example, several divided doses may be administered daily or the dose may be proportionally reduced as indicated by the exigencies of the therapeutic situation.

The active compound may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions that may inactivate the compound.

A compound of the invention can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer a compound of the invention other than by parenteral administration, it may be necessary to coat the compound with, or co-administer the compound with a material to enhance absorption and/or prevent its inactivation. Liposomes include water-in-oil-in-water emulsions as well as conventional liposomes (Strejan et al. (1984) *J. Neiuroimmunol.* 7:27). The active compound may also be administered parenterally or intraperitoneally. Dispersions can also be prepared in glycerol, liquid polyethylene glycols, and mixtures thereof and in oils, and in the form of nanocrystals. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, accepted methods of preparation are vacuum drying and freeze-drying which yields a powder of the active ingredient plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

The following examples are provided for illustrative purposes only and are not intended to limit the scope of the invention which has been described in broad terms above.

EXAMPLE I

Oral Potency of Hexzein

The oral potency of hexzein (7-O-ω-carboxypentyldaidzein) in reducing ethanol intake in Syrian golden hamsters (*Meso cricetus auratus*) was examined under a two-bottle free-choice protocol. Hexzein was mixed with Purina rodent meal (5755M) at 0 mg: 1 g (control), 2 mg: 1 g, 4 mg: 1 g, and 5 mg: 1 g ratios and the mixtures were pressed into 1×1×0.5 inch pellets. Food pellets, ethanol solution and water were provided continuously throughout the study and their intake were measured every day at 5 pm. Hexzein given in this manner did reduce ethanol intake. Ethanol intake in hamsters on 2 mg/g, 4 mg/g, and 5 mg/g hexzein-Chow were reduced by 18.3±3.8%, 47.8±7.4% and 56.5±5.4%, respectively. Daidzin, given in a similar manner and at equivalent dose range, failed to reduce ethanol intake. Tissue distribution studies showed that pharmacologically relevant concentrations of hexzein were found in the liver of hamsters on hexzein-Chow. However, no daidzin could be detected in the liver of hamsters on daidzin-Chow. These results indicated that hexzein is more potent than daidzin and has more desirable pharmacokinetic properties.

EXAMPLE II

Daidzin Mimics Effects of Ethanol Monoamine Metabolism

The effects of daidzin on monoamine metabolism were studied in hamster and rat liver and brain using tissue slices using 5-HT as the substrate. The effects of ethanol drinking on 5-HT metabolism in hamster liver and brain were examined. Freshly removed tissues were cut into small pieces (about 1 mm cubes) with a tissue-slicer, suspended in ice-cold phosphate buffered saline (PBS) (0.1 g/ml), and forced through a mesh 40 stainless steel screen mounted on a Millipore Swinnex Filter Holder. The minced tissues were allowed to sediment on ice before PBS was removed using a Pasteur pipette. The tissue slices were washed 5 more times each with 10 volumes of ice-cold PBS. After the final wash, tissues were suspended in 1 volume of PBS and dispensed using a micro-pipette with tips of i.d.=2 mm. 5-HT metabolism catalyzed by the tissue slices was assayed in a 1 ml assay medium containing PBS, 1 μM 5-HT, 100:1 tissue slices, and specified concentrations of daidzin or ethanol. Reactions were initiated by the addition of tissues and allowed to proceed for 30 min at 37° C. in a shaking water bath. Reactions were terminated by addition of 0.1 ml ice-cold 1 M $HClO_4$, and 10 mM EDTA. Samples were kept on ice for 30 min and centrifuged to obtained clear supernatants. Contents of 5-HT, 5-HIAL, 5-HTOL and 5-HIAA in the supernatants were analyzed by HPLC as described before (Rooke et al. (2000) *J. Med. Chem.* 43:4169).

Daidzin inhibited 5-HIAA formation but not 5-HT depletion in 5-HT metabolism catalyzed by hamster and rat liver slices. Inhibitions were concentration-dependent and accompanied by concomitant increases in the formation of 5-HTOL and other unidentified metabolic products. Ethanol affected 5-HT metabolism in hamster and rat liver slices in a similar manner as daidzin. Daidzin and ethanol did not effect 5-HT metabolism in the brain slices. Daidzin, administered at a dose that would suppress hamster ethanol intake by about 50%, increased urine [5-HTOL]/[5-HIAA] ratio.

EXAMPLE III

Synthesis, Purification, and Structural Identification of Compounds

The 7-O-substituents of the derivatives of daidzein (compounds 2, 4, 6, 8, 11, 13 and 18), puerarin (compounds 17 and 36), 7-hydroxyisoflavone (compounds 3, 5, 7, 9, 10, 12 and 14), 7-hydroxy-2-ethoxycarbonylisoflavone (compounds 15 and 19), 7-hydroxy-4'-fluoro isoflavone (compound 24), 7-hydroxy-4'-bromoisoflavone (compound 26), 7-hydroxy-4-nitroisoflavone (compound 28), and 7-hydroxy-4'-methylisoflavone (compound 30) were synthesized according to the method described in Rooke et al. (2000) *J. Med. Chem.* 43:4169; and Baker and Robinson (1928) *J. Chem. Soc.* 3115. The following 4' substituted derivatives of isoflavone were synthesized: 7-hydroxy-4'-flouroisoflavone (compound 23), 7-hydroxy-4'-bromoisoflavone (compound 25), 7-hydroxy-4'nitroisoflavone (compound 27), 7-hydroxy-4'-methylisoflavone (compound 29), 4',7dimethoxyisoflavone (compound 31), and 7,8-dimethoxyisoflavone (compound 34). The syntheses were based on the formulation of substituted deoxybenzoins as shown in scheme 1, step 1, below, in accordance with teachings of PCT Publication WO 91/15483, and Baker, W.; Chadderton, J.; Harborne, J. B.; Ollis W. D. *A new synthesis of isoflavones*. Part II. *J. Chem. Soc.,* 1953, 1860-1864.

Scheme 1

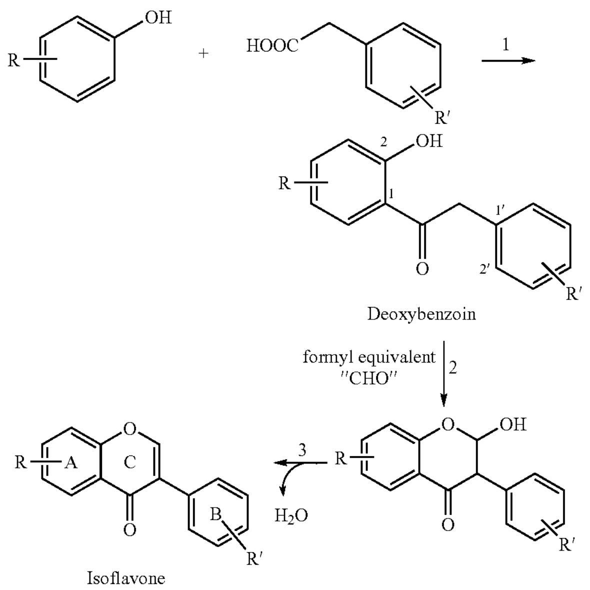

Deoxybenzoins undergo α-keto formylation, intramolecular acetal formation, and a facile dehydration to give the pyrone ring C and hence, the isoflavones as shown in Scheme 1, Step 2 and below. Substituted deoxybenzoins were synthesized by reacting appropriate substituted phenyl acetic acids with properly substituted resorcinols in the presence of $BF_3$. The starting material (7-hydroxy isoflavone, compound 1) for the synthesis of the 7-O-substituted isoflavones was prepared by cyclization of 2,4-dihydroxyphenyl benzyl ketone (Aldrich Chemical Co. Milwaukee, Wis.) as described by WO 91/15483, and shown in steps 2 and 3 of scheme 1, and further described in Gao et al. (2003) Bioorganic & Medicinal Chemistry, in press. 7-Hydroxy-2-ethoxycarbonylisoflavone (compound 20) was prepared by cyclization of the corresponding deoxybenzoin in the presence of an appropriate formyl equivalent as shown in Li, D. Y.; Gao, Z. J.; Ji, Q. E. Synthesis of isoflavones derivatives (I)-7-methoxy-3'-N, N-dialkylaminomethyl-4'-hydroxy isoflavones (*Chinese J. Med. Chem.* 1991, 1 (2), 38-42). The 2-carboxy derivatives (compounds 16, 21, and 22) were obtained by hydrolyzing their respective ethyl esters. The 4'-amino derivatives (compounds 32 and 33) were prepared by reducing their corresponding 4'-nitro derivatives (compounds 27 and 28) under the condition set forth in WO 91/15483, and Li, D. Y.; Gao, Z. J.; Ji, Q. E. Synthesis of isoflavones derivatives (I)-7-methoxy-3'-N, N-dialkylaminomethyl-4'-hydroxy isoflavones. *Chinese J. Med. Chem.* 1991, 1 (2), 38-42. Full explanations of the syntheses are set forth below. All compounds synthesized were purified by Sephadex-LH-20 and/or silica gel columns. Products were identified by $^1$HNMR, $^{13}$C-NMR, MS, and elemental analyses. Purity of all compounds prepared in this study was greater than 97.8% as judged by HPLC with UV detection at 254 mn. Molecular weights, melting points, molecular formulae, and elemental analysis data of these analogs are included in EXAMPLE IV, below.

EXAMPLE IV
Compound Synthesis
Compounds of Formula I were synthesized in accordance with the present invention.
Formula I
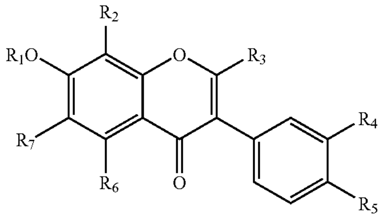
wherein:
| Analog | R1 | R2 | R3 | R4 | R5 | R6 | R7 |
|---|---|---|---|---|---|---|---|
| 1 | H | H | H | H | H | H | H |
| 2 | $CH_3$ | H | H | H | OH | H | H |
| 3 | $CH_3$ | H | H | H | H | H | H |
| 4 | $(CH_3)_2CH—$ | H | H | H | OH | H | H |
| 5 | $(CH_3)_2CH—$ | H | H | H | H | H | H |
| 6 | $C_2H_5OC(O)(CH_2)_5—$ | H | H | H | OH | H | H |
| 7 | $C_2H_5OC(O)(CH_2)_5—$ | H | H | H | H | H | H |
| 8 | $H—(OCH_2CH_2)_3$ | H | H | H | OH | H | H |
| 9 | $H—(OCH_2CH_2)_3$ | H | H | H | H | H | H |
| 10 | $CH_3C(O)—$ | H | H | H | H | H | H |
| 11 | 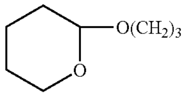 | H | H | H | OH | H | H |
| 12 | 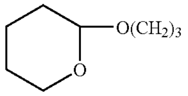 | H | H | H | H | H | H |
| 13 | 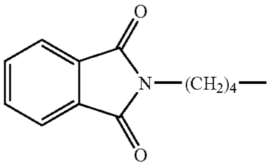 | H | H | H | OH | H | H |
| 14 | 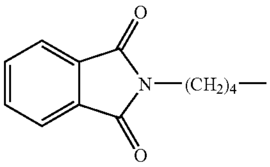 | H | H | H | H | H | H |
| 15 | 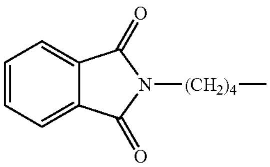 | H | COOEt | H | H | H | H |
| 16 | 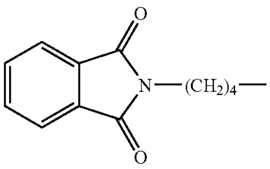 | H | COOH | H | H | H | H |

-continued

Formula I

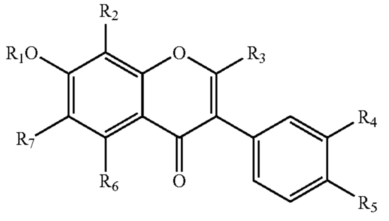

wherein:

| Analog | R1 | R2 | R3 | R4 | R5 | R6 | R7 |
|---|---|---|---|---|---|---|---|
| 17 | 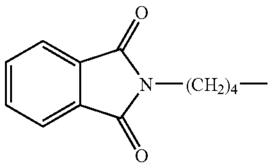 | Glc | H | H | OH | H | H |
| 18 | 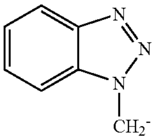 | H | H | H | OH | H | H |
| 19 | 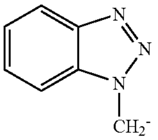 | H | COOEt | H | H | H | H |
| 20 | H | H | COOEt | H | H | H | H |
| 21 | H | H | COOH | H | H | H | H |
| 22 | $HOOC(CH_2)_5$ | H | COOH | H | H | H | H |
| 23 | H | H | H | H | F | H | H |
| 24 | $C_2H_5OC(O)(CH_2)_5$— | H | H | H | F | H | H |
| 25 | H | H | H | H | Br | H | H |
| 26 | $C_2H_5OC(O)(CH_2)_5$— | H | H | H | Br | H | H |
| 27 | H | H | H | H | $NO_2$ | H | H |
| 28 | $C_2H_5OC(O)(CH_2)_5$— | H | H | H | $NO_2$ | H | H |
| 29 | H | H | H | H | $CH_3$ | H | H |
| 30 | $C_2H_5OC(O)(CH_2)_5$— | H | H | H | $CH_3$ | H | H |
| 31 | $CH_3$ | H | H | H | —$OCH_3$ | H | H |
| 32 | H | H | H | H | $NH_2$ | H | H |
| 33 | $CH_3CH_2OC(O)(CH_2)_5$— | H | H | H | $NH_2$ | H | H |
| 34 | $CH_3$— | —$OCH_3$ | H | H | H | H | H |
| 35 | $CH_3CH_2$ | H | H | H | H | H | H |
| 36 | $C_2H_5OC(O)(CH_2)_5$— | Glc | H | H | OH | H | H |
| 37 | $CH_3$ | H | H | H | H | H | Cl |
| 38 | H | H | H | OH | OH | H | H |
| 39 | $CH_3C(O)$— | H | $CH_3$ | H | H | H | H |
| 40 | H | H | H | H | OH | H | H |
| 41 | H | H | H | H | —$OCH_3$ | H | H |
| 42 | Glc | H | H | H | OH | H | H |
| 43 | H | H | H | H | OH | OH | H |
| 44 | Glc | H | H | H | OH | OH | H |
| 45 | $CH_3$— | H | H | H | OH | OH | H |
| 46 | H | H | H | H | —$OCH_3$ | OH | H |
| 47 | Glc | H | H | H | OH | H | —$OCH_3$ |
| 48 | H | Glc | H | H | OH | H | H |
| 49 | $CH_3(CH_2)_5$— | H | H | H | OH | H | H |
| 50 | HO—$(CH_2)_6$— | H | H | H | OH | H | H |
| 51 | $HOOC(CH_2)_{11}$— | H | H | H | OH | H | H |
| 52 | $C_2H_5OOCCH_2$— | H | H | H | OH | H | H |
| 53 | $C_2H_5OOC(CH_2)_4$— | H | H | H | OH | H | H |
| 54 | $HOOC(CH_2)_7$— | H | H | H | OH | H | H |
| 55 | HO—$(CH_2)_9$— | H | H | H | HO—$(CH_2)_9$— | H | H |
| 56 | $HOOC(CH_2)_{15}$— | H | H | H | OH | H | H |
| 57 | HO—$(CH2)_9$— | H | H | H | OH | H | H |
| 58 | $(CH_3)_2CH$— | H | H | H | $(CH_3)_2CH$— | H | H |

-continued

Formula I

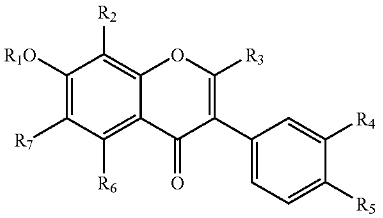

wherein:

| Analog | R1 | R2 | R3 | R4 | R5 | R6 | R7 |
|---|---|---|---|---|---|---|---|
| 60 | $C_2H_5OOC(CH_2)_4$— | H | H | H | $C_2H_5OOC(CH_2)_4$— | H | H |
| 61 | $CH_3(CH_2)_5$— | H | H | H | $CH_3(CH_2)_5$— | H | H |
| 62 | $HOOC(CH_2)_4$— | H | H | H | OH | H | H |
| 63 | HO—$(CH_2)_{12}$— | H | H | H | OH | H | H |
| 65 | $C_2H_5OOC(CH_2)_5$— | H | H | H | $C_2H_5OOC(CH_2)_5$— | H | H |
| 67 | $CH_2$═$CH(CH_2)_4$— | H | H | H | OH | H | H |
| 68 | $CH_2$═$CH(CH_2)_4$— | H | H | H | $CH_2$═$CH(CH_2)_4$— | H | H |
| 69 | $CH_3(CH_2)_{11}$— | H | H | H | OH | H | H |
| 70 | $CH_3(CH_2)_{11}$— | H | H | H | $CH_3(CH_2)_{11}$— | H | H |
| 71 | $C_2H_5OC(O)CH(CH_3)$— | H | H | H | OH | H | H |
| 72 | $C_2H_5OC(O)CH(CH_3)$— | H | H | H | $C_2H_5OC(O)CH(CH_3)$— | H | H |
| 73 | 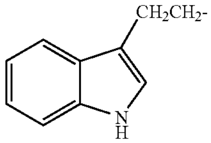 | H | H | H | OH | H | H |
| 74 | $HOC(O)CH(CH_3)$— | H | H | H | OH | H | H |
| 75 | HO-$(CH_2)_2$— | H | H | H | OH | H | H |
| 78 | 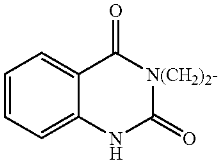 | H | H | H | OH | H | H |
| 79 | 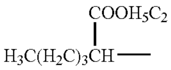 | H | H | H | OH | H | H |
| 80 | 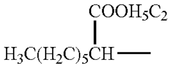 | H | H | H | OH | H | H |
| 81 | 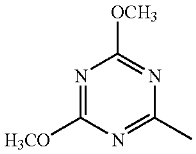 | H | H | H | OH | H | H |
| 82 | 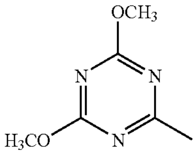 | H | H | H | 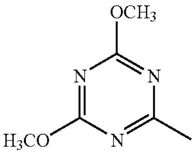 | H | H |
| 83 | 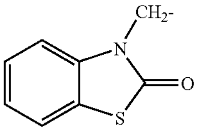 | H | H | H | OH | H | H |

-continued
Formula I
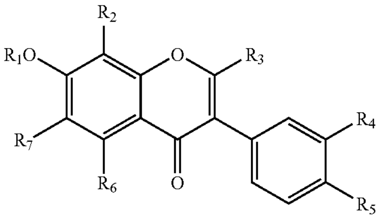
wherein:
| Analog | R1 | R2 | R3 | R4 | R5 | R6 | R7 |
|---|---|---|---|---|---|---|---|
| 85 | 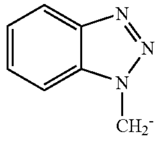 | H | H | H | 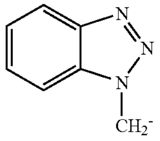 | H | H |
| 86 | H | H | H | H | 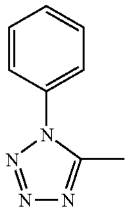 | H | H |
| 87 | 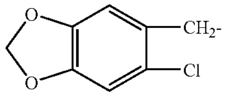 | H | H | H | OH | H | H |
| 88 | 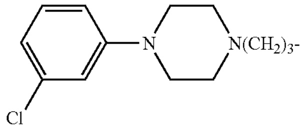 | H | H | H | OH | H | H |
| 89 | 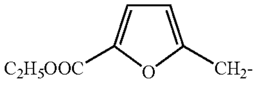 | H | H | H | OH | H | H |
| 90 | 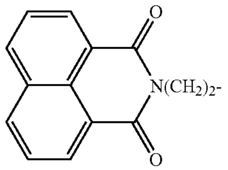 | H | H | H | OH | H | H |
| 99 | 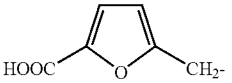 | H | H | H | OH | H | H |

-continued

Formula I

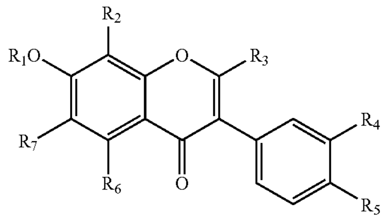

wherein:

| Analog | R1 | R2 | R3 | R4 | R5 | R6 | R7 |
|---|---|---|---|---|---|---|---|
| 106 | 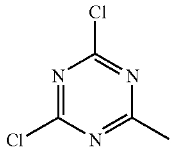 | H | H | H | OH | H | H |

Note:
Glc =

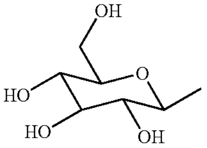

General chemicals were purchased from either Aldrich Chemical Co. (Milwaukee, Wis.) or Lancaster Synthesis Inc. (Windham, N.H.). All organic solvents used were of HPLC grade and were supplied by J. P. Baker (Phillips burg, N.J.) or Fisher Scientific Company (Pittsburgh, Pa.). Daidzin (analog 42) and Glycitin (analog 47) were purchased from LC Laboratories (Woburn, Mass.). Daidzein (analog 40) was first synthesized by Tyger Scientific Inc. (Princeton, N.J.) and later obtained from LC Laboratories. 6-Chloro-7-methylisoflavone (analog 37), 7,3',4'-trihydroxyisoflavone (analog 38), formononetin (analog 41), genistein (analog 43), genistin (analog 44), prunetin (analog 45), biochanin A (analog 46), and puerarin (analog 48) were products of Indofine Chemical Company (Somerville, N.J.). 7-Acetoxy-2-methylisoflavone (analog 39) was purchased from Aldrich (Milwaukee, Wis.). The 7-O-substituted daidzeins (analog 4-analog 8) were prepared in a previous study. Rooke, N.; Li, D. J.; Li, 1. Q.; Keung, W. M. The mitochondrial monoamine oxidase-aldehyde dehydrogenase pathway: a potential site of action of daidzin. *J. Med. Chem.* 2000, 43, 4169-4179. Serotonin (5-HT) was purchased from Research Biochemical International (Natick, Mass.) and its metabolic intermediate 5-HIAL was produced in this laboratory by monoamine oxidase (MAO)-catalyzed oxidative deamination of 5-HT with a rat liver mitochondrial membrane preparation used as a source of MAO. Nilsson, G. E.; Tottmar, O. Biogenic aldehydes in brain: on their preparation and reactions with rat brain tissue (*J. Neurochem.* 1987, 48, 1566-1572). All other reagents used were the best grade available.

$^1$H and $^{13}$C NMR spectra were recorded on a Bruker AMX 500 BQ spectrometer at 500 MHz and Bruker AM-500 spectrometer at 126 MHz (NuMega Resonance Labs. Inc., San Diego, Calif.), respectively, using DMSO as solvent and as internal standard (2.50 and 39.51 ppm for $^1$H and $^{13}$C, respectively) unless otherwise indicated. Mass spectra were measured on a Perkin Elmer PE-SCIEX API 100 mass spectrometer by infusion. Samples were ionized by electro spray and spectra were recorded in positive and negative mode. Melting points were determined with a Hoover capillary melting point apparatus. Elementary analyses were performed by NuMega Resonance Labs. Inc. Crude synthetic' products were purified by one or a combination of the following methods: chromatography on Sephadex LH-20 (Fluka, 25-100 μm) or Silica Gel 60 (70-230 mesh, EM Science) column and recrystallization from acetone or chloroform/methanol of various proportions. Analytical thin layer chromatography (TLC) was performed on Kiselgel $60F_{254}$ plates (Merck KgaA, Darmstadt, Germany).

7-Hydroxyisoflavone (Analog 1)

To a solution of 6.3 g of 2,4-dihydroxyphenyl-benzyl ketone (27.4 mmol) in 10.5 ml of 2-propanol was added 0.5 ml of morpholine and 6 ml of ethyl orthoformate (36.0 mmol). The mixture was stirred at 80° C. for 7 hours and concentrated by flash evaporation. Residue was dissolved in 30 ml of methanol, stirred at 50-60° C. for 20 min and allowed to precipitate at 4° C. for 24 hours. The yellowish precipitates formed were collected by filtration, washed with small portions of methanol and dried to give 5.16 g of amorphous powder (1), a yield of 81.6% (w/w): mp 203-205° C.; 1H NMR (DMSO-$d_6$) δ 6.88 (d, 1H, J=2.0 Hz, 8-H), 6.95 (dd, 1H, J=8.80, 1.90 Hz, 6-H), 7.38 (dd, 1H, J=2.01, 7.24 Hz, 4'-H), 7.42 (dd, IH, J=1.70, 7.30 Hz, 3', 5'-H), 7.57 (dd, IH, J=1.55, 7.84 Hz, 2', 6'-H), 7.97 (d, 1H, J=8.85 Hz, 5-H), 8.38 (s, 1H, 2-H, 10.80 (br. 1H, 7-OH). $^{13}$C NMR (DMSO-$d_6$) δ 102.2 (C-8), 115.3 (C-6), 116.6 (C-10), 123.5 (C-3), 127.3 (C-1'), 127.7 (C-5), 128.1 (C-3', 5'), 128.9 (C-2', 6'), 132.1 (C-4'), 153.8 (C-2), 157.5 (C9), 162.7 (C-7), 174.4 (C-4). MS (m/z) 239.2 $(M+H)^+$, 237.2 (M−H)−. Anal. $(C_{15}H_{10}O_3)$, for C, H. Cacld: 75.62, 4.23; found: 75.62, 4.21.

7-Methoxy-4'-Hydroxyisoflavone (Analog 2)

To a solution of 5.1 g of daidzein (20.06 mmol) in 40 ml of DMSO was added 3.5 g of anhydrous $K_2CO_3$ (25.4 mmol) and 6 ml of iodomethane (96.4 mmol). The mixture was stirred at room temperature for 2 hours and then poured into ice water to precipitate product. Precipitates were extracted with ethyl acetate, dried by flash evaporation and purified on a Sephadex LH-20 column (chloroform:methanol/7:3). Final product was recrystallized from acetone to give 2.3 g of crystalline analog 2, a yield of 45.1% (w/w): mp 210-211° C.; $^1$H NMR (DMSO-$d_6$) δ 3.89 (—$OCH_3$), 6.81 (d, 2H, J=8.43 Hz, 3', 5'-H), 7.05 (dd, 1H, J=8.89, 2.39 Hz, 6-H), 7.11 (d, 1H, J=2.07 Hz, 8-H), 7.39 (d, 2H, J=8.62 Hz, 2', 6'-H), 8.01 (d, 1H, J=8.87 Hz; 5-H), 8.35 (s, 1H, 2-H), 9.54 (s, 1H, 4'-OH). Anal. $(C_{16}H_{12}O_4)$ for C, H. Cacld: 71.64, 4.51; found: 71.24, 4.47.

7-Methoxyisoflavone (Analog 3)

This compound was prepared by the same method as analog 2 using 500 mg of analog 1 instead of daidzein as the starting material. The total product obtained was 515 mg, a yield of 97.1% (mol/mol): mp 156-158° C.; IH NMR (DMSO-$d_6$) δ 3.90 ($OCH_3$), 7.08 (dd, 1H, J=8.94, 2.41 Hz, 6-H), 7.15 (d, 1H, J=2.07 Hz, 8-H), 7.38 (m, 1H, 4'-R), 7.43 (t, 2H, J=7.22, 7.76 Hz, 3', 5'-H), 7.58 (d, 2H, J=7.26 Hz, 2', 6'-H), 8.03 (d, 1H, J=8.86 Hz, 5-H), 8.45 (s, 1H, 2-H). Anal. $(C_{16}H_{12}O_3)$ for C, H. Cacld: 76.26, 4.80; found: 76.07, 4.76.

7-O-Isopropylisoflavone (Analog 5)

To a solution of 2.50 g of analog 1 (10.5 mmol) in 30 ml of DMF was added 1.80 g of anhydrous $K_2CO_3$ (13.0 mmol) and 3.0 ml of 2-bromopropane (32.0 mmol). The mixture was stirred at 80° C. for 4 hours and then poured into ice water. Precipitates were collected by filtration, washed with small portions of water, and dried to give a residue of crude product. The residue was loaded onto a Sephadex LH-20 column (chloroform:methanol, 7:3) and fractions that contained pure product were pooled, concentrated, and recrystallized from acetone to give 1.05 g of crystalline analog 5, a yield of 42% (w/w): mp 110-111° C. $^1$H NMR (DMSO-$d_6$) δ 1.33 (—$CH_3$), 1.34 (—$CH_3$), 4.86 (m, 1H, >$CH_2$—), 7.05 (dd, 1H, J=8.86, 2.20 Hz, 6-H), 7.16 (d, 1H, J=2.50 Hz, 8H), 7.38 (t, 1H, J=6.78 Hz, 4'-H), 7.44 (t, 2H, J=7.76, 1.6 Hz, 3', 5'-H), 7.59 (d, 2H, J=8.09, 1.6 Hz, 2', 6'-H), 8.02 (d, IH, J=8.86 Hz, 5-H), 8.46 (s, 1H, 2-H). $^{13}$C NMR (DMSO-$d_6$) δ 21.5 (—$CH_3$), 21.5 (—$CH_3$), 70.4 (—$CH_2$—O—), 101.8 (C-8), 115.7 (C-6), 117.3 (C-10), 123.7 (C-3), 127.0 (C-1'), 127.8 (C-5), 128.1 (C-3', 5'), 128.9 (C-2', 6'), 132.0 (C4'), 154.0 (C-2), 157.5 (C-9), 162.0 (C-7), 174.1 (C-4). MS (m/z) 281.4 $(M+H)^+$, 303.3 $(M+Na)^+$, 319.4 $(M+K)^+$, 279.5 $(M-H)^-$. Anal. $(C_{23}H_{24}O_5)$ for C, H. Cacld: 77.12, 5.75; found: 76.50, 5.69.

Daidzein 7-ω-Ethoxycarbonylpentyl Ether (Analog 6)

To a solution of 7.7 g of daidzein (30.31 mmol), 30 mL of 2 N aq. KOH (60 mmol) and 120 mL of acetone was added 12.5 mL of ethyl-6-bromo-1-hexanoate (70.60 mmol). The mixture was refluxed with gentle stirring for 72 hours and products were allowed to precipitate over night in the cold room. Precipitates were collected on a flitted funnel and fractionated on a Sephadex LH-20 column in chloroform:methanol (7:3). Fractions that contained pure product were pooled, dried and recrystallized from acetone to give 670 mg of analog 64. Analyses: white crystalline needles: yield 5.6%; mp 130-131° C.; $^1$H NMR (DMSO-$d_6$) δ 1.17 [t, 3H, —$CH_3$], 1.45 (m, 2H, —$CH_2$—), 1.58 (m, 2H, $CH_2$—), 1.74 (m, 2H, —$CH_2$—), 2.31 (t, 2H, —$CH_2$—), 4.04 (m, 2H, —$CH_2$—O—), 4.09 (m, 2H, $CH_2$—O—), 6.82 (dd, 2H, J=9.76 Hz, 2.7 Hz, H-3', H-5'), 7.04 (dd, 1H, J=8.87 Hz, 2.79 Hz, H-6), 7.09 (d, 1H, J=2.1 Hz, H-8), 7.40 (dd, 2H, J=9.76 Hz, 2.7 Hz, H-2', H-6'), 8.0 (d, 1H, J=8.86 Hz, H-5), 8.34 (s, 1H, H-2), 9.55 (s, 1H, OH-4'); $^{13}$C NMR δ 14.1 (—$CH_3$), 24.2 (—$CH_2$—), 24.9 (—$CH_2$—), 28.1 (—$CH_2$—), 33.4 (—$CH_2$—), 59.7 (—$CH_2$—O—), 68.3 (—$CH_2$—O—), 100.9 (C-8), 114.9 (C-6), 115 (C-3', C-5'), 117.5 (C-10), 122.4 (C-1'), 123.7 (C-3), 126.9 (C-5), 130.1 (C-2', C-6'), 153.1 (C-2), 157.2 (C-9), 157.4 (C-4'), 163.0 (C-7), 172.8 (—OCO—), 174.7 (C-4); MS m/z 397.3 $(M+H)^+$. Elementary analysis $(C_{23}H_{24}O_6)$. Cacld: C, 69.68; H, 6.10. Found: C, 69.84; H, 6.15.

7-O-Ethoxycarbonylpentylisoflavone (Analog 7)

This compound was prepared by the same method described for analog 5 except that ethyl 6-bromohexanoate was used as the alkylating agent. From 2.52 g of analog 1, 3.42 g of analog 7 was obtained, a yield of 85% (mol/mol): mp 112-114° C.; $^1$H NMR (DMSO-$d_6$) δ 1.17 (t, 3H, —$CH_3$), 1.45 (m, 2H, —$CH_2$—), 1.60 (m, 2H, —$CH_2$—), 1.77 (m, 2H, $CH_2$—), 2.32 (t, 2H, —$CH_2$—), 4.05 (q, 2H, —$CH_2$—O—), 4.12 (t, 2H, —$CH_2$—O—), 7.07 (dd, 1H, J=8.86, 1.94 Hz, 6-H), 7.16 (d, 1H, J=1.97 Hz, 8-H), 7.38 (dd, 1H, J=7.75, 1.85 Hz, 4'-H), 7.44 (d, 2H, J=7.67 Hz, 3', 5'-H), 7.58 (d, 2H, J=1.94, 7.19 Hz, 2', 6'-H), 8.02 (d, 1H)=8.94 Hz, 5H), 8.47 (s, 1H, 2-H). $^{13}$C NMR (DMSO-$d_6$) δ 14.1 (—$CH_3$), 24.2 (—$CH_2$—), 25.0 (—$CH_2$—), 28.1 (—$CH_2$—), 33.4 (—$CH_2$—), 59.7 (—$CH_2$—O—), 68.4 (—$CH_2$—O—), 101.1 (C-8), 115.1 (C-6), 117.5 (C-10), 123.7 (C-3), 126.9 (C-1'), 127.8 (C-5), 128.1 (C-3', 5'), 128.9 (C-2', 6'), 132.0 (C-4'), 154.1 (C-2), 157.5 (C-9), 163.1 (C-7), 172.8 (>C═O), 174.4 (C-4). MS (m/z) 381.5 $(M+H)^+$, 403.6 $(M+Na)^+$, 419.3 $(M+K)^+$. Anal. $(C_{23}H_{24}O_5)$ for C, H. Cacld: 72.61, 6.36; found: 72.57, 6.33.

7-(Hydroxyethylethoxy)Ethoxyisoflavone (Analog 9)

This compound was prepared by the same method described for analog 5 except that 2-[2-(2-chloroethoxy) ethoxy]ethanol was used as the alkylating agent. From 2 g of analog 1,280 mg of analog 9 was obtained, a yield of 14% (w/w): mp 105-107° C. $^1$H NMR (DMSO-$d_6$) δ 3.43 (m, 2H, —$CH_2$—), 3.50 (m, 2H, —$CH_2$—), 3.56 (m, 2H, —$CH_2$—), 3.61 (m, 2H, —$CH_2$—), 3.80 (m, 2H, —$CH_2$—), 4.26 (m, 2H, —$CH_2$—), 4.58 (t, 2H, —$CH_2$—), 7.10 (dd, 1H, J=8.97, 2.57 Hz, 6-H), 7.18 (d, 1H, J=2.68 Hz, 8-H), 7.37 (t, 1H, J=7.26 Hz, 4' H), 7.44 (t, 2H, J=7.75 Hz, 3', 5'-H), 7.57 (dd, 1H, J=1.60, 7.32 Hz, 2', 6'-H), 8.03 (d, 1H, J=8.88 Hz, 5-H), 8.46 (s, 1H, 2-H). $^{13}$C NMR (DMSO-$d_6$) δ 60.2 (—$CH_2$—), 68.1 (—$CH_2$—), 68.6 (—$CH_2$—), 69.8 (—$CH_2$—), 70.0 (—$CH_2$—), 72.4 (—$CH_2$—), 101.2 (C-8), 115.1 (C-6), 117.8 (C-10), 123.7 (C-3), 126.9 (C-1'), 127.8 (C-5), 128.1 (C-3', 5'), 128.9 (C-2', 6'), 132.1 (C-4'), 154.1 (C-2), 157.4 (C-9), 162.9 (C-7), 174.4 (C-4). MS (m/z) 371.5 $(M+H)^+$, 393.3 $(M+Na)^+$, 409.2 $(M+K)^+$. Anal. $(C_{21}H_{22}O_6)$ for C, H. Cacld: 68.10, 5.99; found: 67.92, 6.05.

7-O-Acetylisoflavone (Analog 10)

To a solution of 500 mg of analog 1 in 15 ml of anhydrous pyridine 2.0 ml of acetic anhydride was added. The mixture was gently stirred for 6 minutes and left at room temperature for 72 hours. Reaction product was precipitated in 100 ml of ice water, collected by filtration, washed with small portions of cold water, and dried under vacuum to give 490 mg of analog 9 (crystalline needle), a yield of 98% (mol/mol): mp 134-135° C. $^1$HNMR (DMSO-$d_6$) δ 2.34 (—$CH_3$), 7.33 (dd, 1H, J=8.47, 2.47 Hz, 6-H), 7.39 (m, 1H, 4'-H), 7.45 (t, 2H, J=7.75 Hz, 3', 5'-H), 7.58 (d, 1H, J=2.3 Hz, 8-H), 7.60 (d, 2H, J=7.75, 1.79 Hz, 2', 6'-H), 8.18 (d, 1H, J=8.86 Hz, 5-H), 8.55 (s, 1H, 2-H). Anal. ($C_{17}H_{12}O_4$) for C, H. Cacld: 72.85, 4.35; found: 72.36, 4.34.

7-O-[Tetrahydro-2-(H)-Pyran-2-O-Propanyl]-Daidzein (Analog 11)

This compound was prepared by the same method described for analog 5 except that daidzein and 2-(3-bromopropoxy)tetrahydro-2H-pyran were used as starting materials. From 5.1 g of daidzein, 4.20 g of analog 11 (white amorphous powder) was obtained, a yield of 82.4% (w/w): mp 112-113° C. $^1$H NMR (DMSO-$d_6$) δ 1.39 (m, 2H, $CH_2$), 1.49 (m, 2H, 3"-H), 1.59-1.71 (m, 2H, 2"-H), 2.01 (m, 2H, —O—$CH_2$—), 3.34-3.53 (m, 2H, 4"-H), 3.70-3.82 (m, 2H, 5"-H), 4.19 (t, 2H, —$CH_2$—O—), 4.58 (d, IH, J=3.62 Hz, 1"H), 6.82 (d, 2H, J=8.53, 2.59, Hz, 3', 5'-H), 7.06 (dd, IH, J=8.86, 2.42 Hz, 6-H), 7.14 (d, 1H, J=2.13 Hz, 8-H), 7.39 (d, 2H, J=8.64 Hz, 2', 6'-H), 8.01 (d, IH, J=8.88 Hz, 5H), 8.35 (s, 1H, 2-H) $^{13}$C NMR (DMSO-$d_6$) δ 19.1 (—$CH_2$—), 25.0 (C-3"), 28.9 (C-4"), 30.2 (C-2"), 61.3 (C-5"), 63.1(—$CH_2$—O—), 65.6 (—$CH_2$—O—), 98.0 (C-1"), 101.0 (C-8), 114.9 (C-6), 114.9 (C-3', 5'), 117.6 (C-10), 122.4 (C-1'), 123.7 (C-3), 126.9 (C-5), 130.0 (C-2', 6'), 153.1 (C-2), 157.2 (C-9), 157.4 (C-4'), 162.9 (C-7), 174.7 (C-4). MS (m/z) 397.2 $(M+H)^+$, 419.4 $(M+Na)^+$, 435.4 $(M+K)^+$, 395.4 $(M-H)^-$. Anal. ($C_{23}H_{24}O_6$) for C, H. Cacld: 69.68, 6.10; found: 69.43, 6.08.

7-O-[Tetrahydro-(2H)-Pyran-2-O-]Propanylisoflavone (Analog 12)

This compound was prepared by the same method described for analog 5 except that 2-(3-bromopropoxy) tetrahydro-2H-pyran was used as the alkylating agent. From 2.38 g of I, 2.67 g of analog 12 (crystalline needle) was obtained, a yield of 70.2% (mol/mol): mp 113-115° C. $^1$H NMR (DMSO-$d_6$) δ 1.41 (m, 2H, —$CH_2$—), 1.47 (m, 2H, 3"-H), 1.59-1.73 (m, 2H, 2"-H), 2.0 (m, 2H, —O—$CH_2$—), 3.40-3.54 (m, 2H, 4"-H), 3.703.83 (m, 2H, 5"-H), 4.21 (t, 2H, —$CH_2$—O—), 4.58 (d, 1H, J=3.5 Hz, 1"-H), 7.08 (dd, 1H, J=8.9, 1.97 Hz, 6-H), 7.17 (d, 1H, J=1.97 Hz, 8-H), 7.38 (t, IH, J=6.98 Hz, 4'-H), 7.43 (t, 2H, J=7.38 Hz, 3', 5'-H), 7.58 (d, 2H, J=7.56 Hz, 2', 6'-H), 8.03 (d, 1H, J=8.88 Hz, 5-H), 8.46 (s, 1H, 2-H). $^{13}$C NMR (DMSO-$d_6$) δ 19.1 (—$CH_2$—), 25.0 (C-3"), 28.9 (C-4"), 30.2 (C-2"), 61.3 (C-5"), 63.1 (—$CH_2$—O—), 65.7 (—$CH_2$—O—), 98.0 (C-1"), 101.1 (C-8), 115.1 (C-6), 117.6 (C-10), 123.7 (C-3), 126.96 (C-1'), 127.8 (C-5), 128.1 (C-3', 5'), 128.9 (C-2', 6'), 132.0 (C-4'), 154.1 (C-2), 157.4 (C-9), 163.1 (C-7), 174.1 (C-4). MS (m/z) 381.4 $(M+H)^+$, 403.4 $(M+Na)^+$, 419.2 $(M+K)^+$, 379.6 $(M-H)^-$. Anal. ($C_{23}H_{24}O_5$) for C, H. Cacld: 72.61, 6.36; found: 72.02, 6.34.

7-O-(Phthalimide-N-)Butyldaidzein (Analog 13)

To a suspension of 5.3 g of daidzein (20.85 mmol) and 50 ml of acetone, 11 ml of 2 N KOH (22 mmol) and 5.6 g of N-(4-bromobutyl)-phthalimide (19.9 mmol) were added. The mixture was stirred under gentle reflux for 72 hours and concentrated. The residue was dissolved in chloroform-methanol (7:3) and loaded onto a Sephadex LH-20 column (chloroform:methanol, 7:3). Fractions that contained pure product were pooled, concentrated, and recrystallized from acetone to give 1.76 g of analog 13, a yield of 33.2% (w/w): mp 195-197° C. $^1$H NMR (DMSO-$d_6$) δ 1.78 (—$CH_2$—$CH_2$—), 3.65 (—N—$CH_2$—), 4.13 (—O—$CH_2$—), 6.81 (d, 2H, J=8.5 Hz, 3', 5'-H), 7.01 (dd, IH, J=8.89, 2.5 Hz, 6-H), 7.07 (d, IH, J=2.2 Hz, 8-H), 7.39 (d, 2H, J=8.6 Hz, 2', 61-H), 7.80 (m, 2H, 5", 6"-H), 7.83 (m, 2H, 4", 7"-H), 7.96 (d, IH, J=8.89 Hz, 5-H), 8.32 (s, 1H, 2-H), 9.54 (s, 1H, 4'OH). $^{13}$C NMR (DMSO-$d_6$) δ 24.6 (—$CH_2$—), 25.8 (—$CH_2$—), 37.1 (—N—$CH_2$—), 67.9 (—$CH_2$—O), 101.0 (C-8), 114.8 (C-6), 114.9 (C-3', 5'), 117.5 (C-10), 122.4 (C-1'), 122.9 (C-3", 8"), 123.6 (C-3), 126.9 (C-5), 130.0 (C-2', 6'), 131.6 (C-5", 6"), 134.3 (C-4", 7"), 153.0 (C-2), 157.2 (C-9), 157.3 (C-4'), 162.8 (C-7), 168.0 (C-2", 9"), 174.6 (C-4). MS (m/z) 456.5 $(M+H)^+$. Anal. ($C_{27}H_{21}O_6N$) for C, H, N. Cacld: 71.20, 4.65, 3.08; found: 70.89, 4.61, 3.09.

Isoflavone 7-ω-(N-phthalimidylbutyl) Ether (Analog 14)

To a suspension of 1.6 g of 7-hydroxyisoflavone (6.7 mmol) in 50 ml of acetone was added 7 ml of 2 N aq. KOH (14 mmol). The resulting mixture was stirred at room temperature until all starting materials were dissolved. To this solution, 4.4 g (15.6 mmol) of N-4-bromobutylphthalimide was added and the reaction mixture was stirred under gentle reflux for 72 hours and left in the cold room overnight. Precipitates were collected by filtration and recrystallized from acetone to give 1.26 g analog 76. Analyses: colorless crystals; yield 78.5%, w/w; mp 167-168° C. $^1$H NMR (DMSO-$d_6$) δ 1.78 (—$CH_2$—$CH_2$—), 3.65 (—N—$CH_2$—), 4.14 (—O—$CH_2$—), 7.03 (dd, 1H, J=8.9, 2.0 Hz, H-6), 7.10 (d, 1H, J=1.8 Hz, H-8), 7.37 (dd, 1H, J=6.92 Hz, H-4'), 7.42 (dd, 2H, J=7.7 Hz, H-3', 5'), 7.57 (dd, 2H, J=7.6, H-2', 6"), 7.83 (m, 2H, 4", H-7"), 7.96 (d, 1H, J=8.89 Hz, H-5), 8.32 (s, 1H, H-2), 9.54 (s, 1H, OH-4'). $^{13}$C NMR (DMSO$d_6$) δ 24.6 (—$CH_2$—), 25.8 (—$CH_2$—), 37.1 (—N—$CH_2$—), 67.9 (—$CH_2$—O—), 101.0 (C-8), 115.0 (C6), 117.5 (C-10), 122.9 (C-3", 8"), 123.7 (C-3), 126.9 (C-1'), 127.8 (C-5), 128.1 (C-3', 5'), 128.9 (C-2', 6'), 131.6 (C-5", 6"), 132.0 (C-4'), 134.3 (C-4", 7"), 154.1 (C-2), 157.4 (C-9), 163.0 (C-7), 168.0 (C-2", 9"), 174.6 (C-4). MS (m/z) 440.1 $(M+H)^+$. Elementary analyses ($C_{27}H_{21}O_5N$) for C, H, N: Cacld. 73.79, 4.82, 3.19; found 73.40, 4.81, 3.20.

2-Ethoxycarbonyl-7-O-Phthalimide-N-Butylisoflavone (Analog 15)

To a solution of 2.53 g (8.16 mmol) of analog 20 (see below for method of synthesis) in 50 ml of DMF, 1.59 g of $K_2CO_3$ (11.49 mmol) and 3.0 g of N-4bromobutylphthalimide (10.63 mmol) were added, respectively. The mixture was stirred at 80° C. for 1 hour and then poured into ice water. Precipitates were collected by filtration, washed with small portions of water, dried, and recrystallized in acetone to give 3.85 g of analog 15, a yield of 92.2% (mol/mol): mp 163-165° C. $^1$H NMR (DMSO-$d_6$) δ 0.90 (—$CH_3$), 1.78 (—$CH_2$—$CH_2$—), 3.65 (—N—$CH_2$—), 4.08 (—O—

$CH_2$—), 4.16 (—O—$CH_2$—), 7.05 (dd, IH, J=8.97, 2.42 Hz, 6-H), 7.16 (d, 1H, J=2.44 Hz, 8-H), 7.24 (d, 2H, J=8.53 Hz, 3', 5'-H), 7.39 (m, 3H, 2', 4', 6'-H), 7.79-7.81 (m, 2H, 5", 6"-H), 7.82-7.85 (m, 2H, 4", 7"H), 7.92 (d, 1H, J=8.89 Hz, 5-H). $^{13}C$ NMR (DMSO-$d_6$) δ 13.2 (—$CH_3$), 24.5 (—$CH_2$—), 25.8 (—$CH_2$—), 37.1 (—N—$CH_2$—), 62.1 (—$CH_2$—O—), 68.1 (—$CH_2$—O—), 101.0 (C-8), 115.9 (C-6), 116.7 (C-10), 122.9 (C-3", 8"), 125.2 (C-1'), 126.9 (C-3), 127.8 (C-3', 5'), 127.9 (C—S), 129.7 (C-2', 6'), 131.5 (C-5", 6"), 134.3 (C-4", 1"), 150.0 (C-2), 156.7 (C-9), 160.9 (>C═O), 163.7 (C-7), 168.0 (C-2", 9"), 175.3 (C-4). MS (m/z) 533.7 $[(M-1)+Na]^+$, 549.6 $[(M-1)+K]^+$, 4.39.1 $[M-COOC_2H_5-1]^-$. Anal. ($C_{30}H_{25}O_7N$) for C, H, N. Cacld: 70.44, 4.93, 2.74; found: 70.35, 4.92, 2.76.

2-Carboxy-7-O-Phthalimide-N-Butylisoflavone (Analog 16)

This compound was prepared by hydrolyzing analog 15. To a solution of 1.0 g of analog 15 in 20 ml of methanol was added 80 ml of 0.02 N aqueous KOH. The mixture was stirred under gentle reflux for 3 hours until all samples were hydrolyzed (TLC). Methanol was removed by flash evaporation. The remaining solution was acidified with 1 N HCl to pH 2-3 to precipitate produce. Precipitates were collected by filtration and washed with small portions of water until pH of filtrate became neutral. The solution was then dried and residue was recrystallized from acetone to give 630 mg of analog 16 (white crystals): mp 143-145° C. MS (m/z) 484.5 $(M+H)^+$, 506.4 $(M+Na)^+$, 482.5 $(M-H)^-$. Anal. ($C_{28}H_{21}O_7N$) for C, H, N. Cacld: 69.56, 4.38, 2.90; found: 69.56, 4.42, 2.89.

7-O-Phthalimide-N-Butylpuerarin (Analog 17)

This compound was prepared by the same method described for analog 13 except that puerarin was used instead of daidzein. From 500 mg of puerarin, 512 mg of analog 17 (white powder) was obtained, a yield of 69.0%: mp 68-69° C. $^1H$ NMR (DMSO-$d_6$) δ 1.78 (—$CH_2$—$CH_2$—), 3.65 (—N—$CH_2$—), 4.14 (—O—$CH_2$—), 4.82 (d, 1H, J=9.7 Hz, glucosyl 1'"-H), 7.03 (dd, 1H, J=8.9, 2.0 Hz, 6-H), 7.10 (d, 1H, J=1.8 Hz, 8-H), 7.37 (dd, 1H, J=6.92 Hz, 4'-H), 6.81 (dd, 2H, J=7.7 Hz, 3', 5'-H), 7.41 (dd, 2H, J=7.6, 2', 6'-H), 7.80 (m, 2H, 5", 6"-H), 7.83 (m, 2H, 4", 7"-H), 7.96 (d, 1H, J =8.89 Hz, 5-H), 8.40 (s, 1H, 2H), 9.54 (s, 1H, 4'-OH). $^{13}C$ NMR (DMSO-$d_6$) δ 24.6 (—$CH_2$—), 25.8 (—$CH_2$—), 37.1(—$NCH_2$—), 61.5 (glucosyl C-6'"), 67.9 (—$CH_2$—O—), 70.7 (glucosyl C-4'"), 70.75 (glucosyl C2'"), 73.39 (glucosyl C-1'"), 78.71 (glucosyl C-3'"), 81.79 (glucosyl C-5'"), 112.6 (C-8), 115.0 (C-6), 117.5 (C-10), 122.9 (C-3", 8"), 123.7 (C-3), 126.9 (C-1'), 127.8 (C-5), 128.1 (C-3', 5'), 128.9 (C-2', 6'), 131.6 (C-5", 6"), 132.0 (C-4'), 134.3 (C-4", 7"), 154.1 (C-2), 157.4 (C-9), 163.0 (C-7), 168.0 (C-2", 9"), 174.6 (C-4). MS (m/z) 618.4$(M+H)^+$, 640.5 $(M+Na)^+$, 616.7 $(M-H)^-$. Anal. ($C_{33}H_{31}O_{11}N$) for C, H, N. Cacld: 64.18, 5.06, 2.27; found: 63.89, 5.05, 2.24.

Daidzein 7-O-1H-Benzotriazole-1-Methyl ether (Analog 18)

This compound was prepared by the same method described for analog 5 except that daidzein and 1-chloromethyl-1H-benzotriazole were used as the starting material. From 5.1 g of daidzein, 4.35 g of analog 18 was obtained, a yield of 85.3% (w/w): mp 227-228° C. $^1H$ NMR (DMSO-$d_6$) δ 6.83 (dd, 2H, J=8.63, 2.62 Hz, 3', 5'-H), 6.98 (s, 2H, —$CH_2$—), 7.21 (dd, 1H, J=8.89, 2.31 Hz, 6-H), 7.41 (dd, 2H, 2', 6'-H), 7.8 (t, 1H, J=7.84 Hz, 1"-H), 7.54 (d, 1H, J=2.02 Hz, 8-H), 7.66 (t, 1H, J=7.69, 2.02 Hz, 4"-H), 8.03 (t, 1H, J=8.85, 8.04 Hz, 2", 3"-H), 8.11 (d, 1H, J=8.52 Hz, 5-H), 8.40 (s, 1H, 2-H), 9.56 (s, 1H, 4'-OH). $^{13}C$ NMR (DMSO-$d_6$) δ 73.7 (—N—$CH_2$—O—), 103.2 (C-8), 110.7 (C1"), 115.0 (C-3', 5'), 115.4 (C-6), 118.9 (C-4"), 119.5 (C-10), 122.2 (C-1'), 123.8 (C-3), 124.8 (C-2"), 127.3 (C-5), 128.5 (C-3"), 130.1 (C-2', 6'), 132.7 (C-6"), 145.3 (C-5"), 153.4 (C-2), 156.9 (C-9), 157.3 (C-4'), 159.9 (C-7), 174.7 (C-4). MS (m/z), 386.4 $(M+H)^+$. Anal. ($C_{29}H_{20}O_4N_3$) for C, H, N, Cacld: 68.57, 3.92, 10.90, found: 68.28, 3.92, 10.94.

2-Ethoxycarbonyl-7-O-1H-Benzotriazole-1-Methyl-isoflavone (Analog 19)

This compound was prepared by the same method described for analog 18 except that analog 20 (see below for method of synthesis) was used instead of daidzein. From 3.1 g of analog 20, 1.43 g of analog 19 was obtained, a yield of 46% (w/w): mp 182-183° C. $^1H$ NMR (DMSO-$d_6$) δ 0.92 (—$CH_3$), 4.09 (—$CH_2$—O—), 7.03 (s, 2H, —N—$CH_2$—O—), 7.23 (dd, 1H, J=8.78, 2.79 Hz, 6-H), 7.25 (dd, 2H, J=8.78, 2.77 Hz, 3', 5'-H), 7.40 (dd, 2H, J=8.53, 1.50 Hz 2', 6'-H), 7.40 (d, 1H, J=1.5 Hz, 8-H), 7.49 (t, 1H, J=7.99, 7.46 Hz, 4'H), 7.65-7.68 (m, 2H, 1", 4"-H), 7.99-8.04 (m, 2H, 2", 3"-H), 8.12 (d, IH, J=8.38 Hz, 5H). $^{13}C$ NMR (DMSO-$d_6$) δ 13.2 (—$CH_3$), 62.1 (—$CH_2$—O—), 73.6 (—N—$CH_2$—O—), 103.2 (C8), 110.7 (C-1"), 116.3 (C-6), 118.1 (C-10), 119.5 (C-4"), 124.8 (C-3), 125.5 (C-1'), 127.3 (C-5), 127.8 (C-3', 5'), 128.0 (C-2"), 128.6 (C-3"), 129.7 (C-2', 6'), 131.4 (C-6"), 132.7 (4'-H), 145.3 (C-5"), 150.1 (C-2), 156.3 (C-9), 160.8 (>C═O, C-7), 175.5 (C-4). MS (m/z) 442.2 $(M+H)^+$, 463.9 $(M+Na)^+$, 479.8 $(M+K)^+$. Anal. ($C_{25}H_{19}O_5N_2$) for C, H, N. Cacld: 68.02, 4.34, 9.52; found: 68.66, 4.36, 9.58.

2-Ethoxycarbonyl-7-Hydroxyisoflavone (Analog 20)

To a solution of 4.56 g of 2,4-dihrdroxyphenylbenzylketone (20.24 mmol) in 20 ml of pyridine was added 3.5 ml of ethyl chlorooxoacetate (31.28 mmol). The mixture was stirred gently at room temperature for 1 hour and yellowish precipitates were fanned. The precipitates were collected by filtration and dried, redissolved in chloroform:methanol (7:3), and loaded onto a Sephadex LH-20 (chloroform: methanol, 7:3) column. Fractions that contained pure product were pooled, concentrated and recrystallized from acetone to give 4 g of analog 20, a yield of 87.61%: mp 213-214° C. 1H NMR (DMSO-$d_6$) δ 0.88 (t, 3H, —$CH_3$), 4.05 (—$CH_2$—), 6.90 (d, 1H, J=1.91 Hz, 8-H), 6.98 (dd, 1H, J=8.82, 1.91 Hz, 6-H), 7.23 (d, 1H, J=7.15 Hz, 3', 5'-H), 7.39-7.42 (m, 3H, 2', 4', 6'-H), 7.92 (d, 1H, J=8.84 Hz, 5-H), 11.02 (s, 1H, 7-OH). $^{13}C$ NMR (DMSO-$d_6$) d 13.2 (—$CH_3$), 62.0 (—$CH_2$—O—), 102.2 (C-8), 115.9 (C-6), 115.9 (C-10), 125.1 (C-1'), 127.4 (C-3), 127.8 (C-3', 5'), 127.9 (C-5), 129.8 (C-2', 6'), 131.7 (C-4'), 149.8 (C-2), 156.8 (C-9), 161.0 (>C═O), 163.5 (C-7), 175.3 (C-4). MS (m/z) 311.3 $(M+H)^+$, 333.1 $(M+Na)^+$, 309.2 $(M-H)^-$. Anal. ($C_{18}H_{14}O_5$) for C, H. Cacld: 69.67, 4.55; found: 69.27, 4.59.

2-Carboxy-7-Hydroxyisoflavone (Analog 21)

This compound was obtained by hydrolyzing analog 20. To a solution of 1 g of analog 20 in 10 ml of methanol was added 20 ml of 0.2 N aqueous KOH. The mixture was stirred under gentle reflux for 2 hours until analog 20 was completely hydrolyzed (monitored by TLC). Methanol was removed on a rotary evaporator. Hydrolyzed product in remaining solution was precipitated by acidification (HCl, pH 2-3). Precipitates were collected by filtration, washed with small portions of water until pH of filtrate approached neutral, and recrystallized from acetone to give 630 mg of pure analog 21, a yield of 63% (w/w): mp 257-258° C. MS (m/z) 283.2 $(M+H)^+$, 305.3 $(M+Na)^+$, 321.3 $(M+K)^+$, 237.4 $(M-COOH)^+$, 281.5 $(M-H)^-$. Anal. $(C_{16}H_{10}O_5)$ for C, H. Cacld: 68.09, 3.57; found: 68.17, 3.54.

2-Carboxy-7-ω-Carboxylpentyl Isoflavone (Analog 22)

To a solution of 5.0 g (16.1 mmol) of analog 20 in 60 ml of DMF was added 2.6 g of $K_2CO_3$ (18.8 mmol) and 3 ml of ethyl6-bromo hexanoate (16.86 mmol). The mixture was refluxed for 1 hour and poured into 100 ml of ice water. Products were extracted with ethyl acetate and evaporated to dryness. Dry residue was dissolved in 20 ml of methanol followed by addition of 20 ml of 1N KOH (20 mmol). The mixture was stirred under gentle reflux for 2 hours until the ethyl ester was completely hydrolyzed (monitored by TLC). Solvent was removed under reduced pressure. Residue was dissolved in chloroform-methanol (7:3) and purified on a Sephadex-LH-20 column in chloroform:methanol (7:3). Fractions that contained pure product were pooled, concentrated and recrystallized from acetone to give 5.34 g of analog 22, a yield of 83.7%: mp 157-159° C. $^1H$ NMR (DMSO-$d_6$) δ 1.44 (m, 2H, —$CH_2$), 1.60 (m, 2H, —$CH_2$), 1.76 (m, 2H, —$CH_2$), 2.33 (m, 2H, —$CH_2$), 4.14 (—$CH_2$—), 7.09 (d, 1H, J=1.8 Hz, 6-H), 7.21 (d, 1H, J=2.5 Hz, 8-H), 7.26 (dd, 1H, J=7.54, 1.52 Hz, 3', 5'-H), 7.34-7.41 (m, 3H, 2', 4', 6'-H), 7.96 (d, 1H, J=8.88 Hz, 5-H).13C NMR (DMSO-$d_6$) 8 24.1 (—$CH_2$), 24.9 ($CH_2$), 28.0 (—$CH_2$), 33.1 (—$CH_2$), 33.4 (—$CH_2$), 68.5 (—$CH_2$—O—), 101.0 (C-8), 115.8 (C-6), 116.7 (C-10), 123.9 (C-1'), 126.9 (C-3), 127.8 (C-31, 51), 127.9 (C-5), 129.8 (C-2', 6'), 131.7 (C-41), 151.7 (C-2), 156.8 (C-9), 162.3 (>C═O), 163.8 (C-7), 173.3 (C-4), 175.5 (C-4). Anal. $(C_{22}H_{20}O_7)$ for C, H. Cacld: 66.67, 5.09; found: 66.89, 5.14.

7-Hydroxy-4'-Fluoroisoflavone (Analog 23)

A mixture of 1.54 g of 4-fluorophenylacetic acid (90.5 mmol), 11.0 g of resorcinol (99.9 mmol) and 50ml of boron trifluoride diethyl etherate was stirred at 80° C. for 5 hours. The reaction mixture was cooled to room temperature and then washed rust with aqueous $K_2CO_3$ and then with water until pH of the water layer approached 7. The product was extracted with ethyl acetate and concentrated. The residue was dissolved and loaded onto a Sephadex-LH-20 column (chloroform:methanol, 7:3). Fractions that contained pure analog 23 were pooled and dried to give 3.5 g of crude 2,4dihydroxyphenyl-4'-fluorobenzylketone (I). To 3.5 g on in 20 ml of 2-propanol was added 1.0 ml of morpho line and 2.5 ml of triethyl orthoformate. The mixture was stirred at 80° C. for 7 hours. Solvents were removed and residue was dissolved in 30 ml of methanol and stirred at 50° C. for 30 min. The solution was cooled to room temperature and kept at 4° C. overnight. White crystals were collected by filtration, washed with small portions of methanol, and dried to give 1.53 g of analog 23, a yield of 43.7% (w/w): mp 235-236° C. $^1H$ NMR (DMSO-$d_6$) δ 6.88 (d, 1H, J=1.73 Hz, 8-H), 6.95 (dd, 1H, J=8.80, 1.85 Hz, 6-H), 7.25 (t, 2H, J=8.82 Hz, 3', 5'-H), 7.61(dd, 2H, J=2.52, 8.21 Hz, 2', 6'-H), 7.97 (d, 1H, J=8.80 Hz, 5-H), 8.40 (s, 1H, 2-H), 10.8 (s. 1H, 7-OH). $^{13}C$ NMR (DMSO-$d_6$) δ 102.2 (C-8), 114.9 (C-6), 115.0 (C-3', 5'), 116.5 (C-10), 122.5 (C-1'), 127.3 (C-3), 128.4 (C-5), 130.9 (C-2', 6'), 153.8 (C-2), 157.5 (C-9), 160.8 (C-4'), 162.7 (C-7), 174.3 (C-4). MS (m/z) 257.2 $(M+H)^+$, 279.3 $(M+Na)^+$, 255.4 $(M-H)^-$. Anal. $(C_{15}H_9O_3F)$ for C, H. Cacld: 70.31, 3.54; found: 70.56, 3.51.

7-O-Ethoxycarbonylpentyl-4'-Fluoroisoflavone (Analog 24)

This compound was prepared by the same method described for analog 5 except that the starting materials were analog 23 and ethyl 6-bromohexanoate. From 1.28 g of analog 23, 964 mg of analog 24 (crystalline needles) was obtained, a yield of 75.3% (w/w): mp 91-93° C. $^1H$ NMR (DMSO-$d_6$) δ 1.16 (t, 3H, —$CH_3$), 1.43 (m, 2H, —$CH_2$—), 1.60 (m, 2H, —$CH_2$—). 1.76 (m, 2H, —$CH_2$—), 2.31 (t, 2H, —$CH_2$—), 4.05 (q, 2H, —$CH_2$—O—), 4.10 (t, 2H, —$CH_2$—O—), 7.05 (d, 1H, J=8.88, Hz, 6-H), 7.14 (d, 1H, J=1.97 Hz, 8-H), 7.26 (d, 2H, J=8.78 Hz, 3', 5'-H), 7.63 (t, 2H, J=8.78 Hz, 2', 6'-H), 8.01 (d, 1H, J=8.84 Hz, 5-H), 8.46 (s, 1H, 2-H). $^{13}C$ NMR (DMSO-$d_6$) δ 14.1 (—CH3), 24.2 (—$CH_2$—), 24.9 (—$CH_2$—), 28.1 (—$CH_2$—), 33.4 (—$CH_2$—), 59.6 (—$CH_2$—O—), 68.3 (—$CH_2$—O—), 101.0 (C-8), 114.9 (C-6), 115.0 (C-3', 5'), 117.4 (C-10), 122.7 (C-1'), 126.9 (C-3), 128.3 (C-5), 130.9 (C-2', 6'),154.1 (C-2), 157.4 (C-9), 160.9 (C-4'), 163.1 (C-7), 172.8 (>C═O), 174.3 (C-4). MS (m/z) 399.4 $(M+H)^+$, 421.4 $(M+Na)^+$. Anal. $(C_{23}H_{23}O_5F)$ for C, H. Cacld: 69.34, 5.82; found: 69.23, 5.79.

7-Hydroxy-4'-Bromoisoflavone (Analog 25)

The synthesis was similar to that described for analog 23 except that 4fluorophenylacetic acid was replaced with 4-bromophenylacetic acid. This synthesis resulted in 1.41 g of analog 25, a yield of 42% (based on resorcinol, w/w): mp 266-268° C. $^1H$ NMR (DMSO-$d_6$) δ 6.87 (d, 1H, J=1.65 Hz, 8-H), 6.94 (dd, 1H, J=8.80, 1.78 Hz, 6-H), 7.54 (d, 2H, J=8.43 Hz, 3', 5'-H), 7.61 (d, 2H, J=8.43 Hz, 2" 6'-H), 7.97 (d, 1H, J=8.63 Hz, 5-H), 8.42 (s, 1H, 2-H), 10.8 (s, br. 1H, 7-OH). $^{13}C$ NMR (DMSO-$d_6$) δ 102.2 (C-8), 115.4 (C-6), 116.4 (C-10), 121.0 (C-1'), 122.3 (C-3), 127.3 (C-5), 130.9 (C 3',51),131.0 (C-2', 6'),131.4 (C-4'), 154.0 (C-2), 157.5 (C-9), 162.7 (C-7), 174.1 (C-4). MS (m/z) 317.1 $(M)^+$, 340.8 $(M+Na)^+$. Anal. $(C_{15}H_9O_3Br)$ for C, H. Cacld: 56.81, 2.86; found: 56.56, 2.85.

4'-Bromoisoflavone 7-ω-Ethoxycarbonylpentyl Ether (Analog 26)

A reaction mixture containing 4.36 g of 4-bromophenylacetic acid (20.3 mmol), 3.36 g of resorcinol (30.5 mmol) and 50 ml of boron trifluoride diethyl etherate was stirred at 80° C. for 5 h. The reaction mixture was cooled to room temperature and then washed with aqueous $K_2CO_3$ followed by water until pH of the water layer reached ≈7. The product was extracted with ethyl acetate and concentrated by flash evaporation. Residue was dissolved and fractionated on a Sephadex-LH-20 column (chloroform:methanol/7:3). Fractions that contained the pure product 2,4-dihydroxyphenyl-4'-bromobenzylketone were pooled and evaporated to dryness. To this residue, 50 ml of 2-propanol, 7.0 ml of morpholine and 10 ml of triethyl orthoformate were added. The reaction mixture was stirred at 80° C. for 24 h. Solvents were evaporated and residue was dissolved in 20 ml of methanol and stirred at 50° C. for another 20 min. The solution was cooled to room temperature and kept at 4° C. overnight. The yellow precipitates of 4'-bromo-7-hydroxy-lisoflavone was collected by filtration (2.8 g). The precipitate was dissolved in 50 ml of DMF and to this solution was added 2.76 g of $K_2CO_3$ (20.0 mmol), followed by 6.0 ml of ethyl 6-bromohexanoate (33.7 mmol). The mixture was stirred and heated at 80° C. for 3.5 h and poured into 200 ml of ice water. Precipitates formed were collected by filtration and fractionated on a Sephadex LH-20 column (chloroform: methanol/7:3). Fractions that contained purified product were pooled, concentrated and recrystallized from acetone to give 1.62 g pure analog 104. Analyses: white crystals; yield, 57.1%; mp 122-124° C. $^1$H NMR (DMSO-$d_6$) δ 1.17 (t, 3H, —$CH_3$), 1.43 (m, 2H, —$CH_2$—), 1.60 (m, 2H, —$CH_2$—), 1.76 (m, 2H, —$CH_2$—), 2.31 (m, 2H, —$CH_2$—), 4.04 (q, 2H, —$CH_2$—O—), 4.11 (t, 2H, —$CH_2$—O—), 7.06 (dd, 1H, J=8.88, 2.56 Hz, H-6), 7.15 (d, 1H, J=1.93 Hz, H-8), 7.55 (d, 2H, J=8.68 Hz, H-3', 5'), 7.62 (d, 2H, J=8.68 Hz, H-2',6'), 8.01 (d, 1H, J=8.87 Hz, H-5), 8.50 (s, 1H, H-2). $^{13}$C NMR (DMSO-$d_6$) δ 14.1 (—$CH_3$), 24.1 (—$CH_2$—), 24.9 (—$CH_2$—), 28.0 (—$CH_2$—), 33.4 (—$CH_2$—), 59.6 ($CH_2$—O—), 68.4 (—$CH_2$—O—), 101.0 (C-8), 115.2 (C-6), 117.4 (C-10), 121.1 (C-1'), 122.5 (C3),126.9 (C-5), 130.9 (C-3', 5'), 131.0 (C-2', 6'), 131.2 (C-4'), 154.3 (C-2), 157.4 (C-9), 163.2 (C-7), 172.8 (>C═O), 174.1 (C-4). MS (m/z), 460.0 (M+H)+. Elementary analyses ($C_{23}H_{23}O_5Br$) for C, H: Cacld: 60.14, 5.05; found: 59.74, 4.66.

7-Hydroxy-4'-Nitroisoflavone (Analog 27)

This compound was prepared by the same method described for analog 23 except that the starting material4-fluorophenylacetic acid was replaced by 4-nitrophenyl acetic acid. A total of 1.35 g of analog 27 was obtained, a yield of 38.6% (w/w): mp 270° C. (decomposes). $^1$H NMR (DMSO-$d_6$) δ 6.86 (d, 1H, J=2.0 Hz, 8-H), 6.94 (dd, 1H, J=8.84, 1.93 Hz, 6-H), 7.88 (d,2H, J=8.76,1.48 Hz, 2', 6'-H), 7.97 (d, 1H, J=8.79 Hz, 5H), 8.27 (d, 2H, J=8.78, 1.70 Hz, 3', 51-H), 8.56 (s, 1H, 2-H). $^{13}$C NMR (DMSO-$d_6$) δ 102.3 (C-8), 115.9 (C-6), 116.0 (C-6), 116.0 (C-10), 121.5 (C-3), 123.2 (C-2', 6'), 127.3 (C-5), 129.9 (C-31, 51), 139.4 (C-1'), 146.7 (C-4), 155.3 (C-2), 157.5 (C-9), 163.8 (C-7), 173.8 (C-4). MS (m/z) 283.9 ($M^+$), 306.3 $(M+Na)^+$, 282.4 $(M-H)^-$. Anal. ($C_{15}H_9O_5N$) for C, H, N. Cacld: 63.61, 3.20, 4.95; found: 63.48, 3.21, 4.91.

7-O-Ethoxycarbonylpentyl-4'-Nitroisoflavone (Analog 28)

This compound was prepared by the same method described for analog 24 except that analog 27 was used as the starting material. A total of 270 mg analog 28 was obtained from this synthesis, a yield of 13.5% (w/w): mp 173-175° C. $^1$H NMR (DMSO-$d_6$) δ 1.17 (t, 3H, —$CH_3$), 1.44 (m, 2H, —$CH_2$—), 1.59 (m, 2H, —$CH_2$—), 1.60 (—$CH_2$—), 1.77 (—$CH_2$—), 2.32 (—$CH_2$—), 4.04 (—$CH_2$—O—), 4.13 (—$CH_2$—O—), 7.10 (dd, 1H, J=8.85, 1.94 Hz, 6-H), 7.20 (d, 1H, J=2.32 Hz, 8-H), 7.92 (d, 2H, J=8.73 Hz, 2', 6'-H), 8.04 (d, 1H, J=8.87 Hz, 5-H), 8.29 (d, 2H, J=8.74 Hz, 3', 5'-H), 8.68 (s, 1H, 2-H). $^{13}$C NMR (DMSO-$d_6$) δ 14.1 (—$CH_3$), 24.2 (—$CH_2$—), 24.9 (—$CH_2$—), 28.0 (—$CH_2$—), 33.4 (—$CH_2$—), 59.7 ($CH_2$—O—), 68.4 (—$CH_2$—O—), 101.2 (C-8), 115.4 (C-6), 117.4 (C-10), 121.8 (C-3), 123.2 (C2', 6'), 126.9 (C-5), 129.9 (C-3', 5'), 139.1 (C-1'), 146.7 (C-4'), 155.7 (C-2), 157.4 (C-9), 163.4 (C-7), 172.8 (—C═O), 173.9 (C-4). Anal. ($C_{23}H_{23}O_7N$) for C, H, N. Cacld: 64.93, 5.54, 3.29; found: 64.63, 5.48, 3.31.

7-Hydroxy-4'-Methylisoflvone (Analog 29)

This compound was prepared by a similar method described for analog 23 except that 4-flurophenylacetic acid was replaced by p-tolylacetic acid. A total of 780 mg analog 29 was obtained from this procedure, a yield of 21.3% (based on resorcinol, w/w): mp 241-243° C. $^1$H NMR (DMSO-$d_6$) δ 2.33 (s, 3H, —$CH_3$), 6.87 (d, $^1$H, J=1.94 Hz, 8-H), 6.94 (dd, 1H, J=8.72, 2.68 Hz, 6-H), 7.21 (t, 2H, J=7.92 Hz, 3', 5'-H), 7.45 (d, 2H, J=8.28 Hz, 2', 6'-H), 7.97 (d, 1H, J=8.85 Hz, 5-H), 8.33 (s, 1H, 2-H). $^{13}$C NMR (DMSO-$d_6$) δ 20.8 (—$CH_3$), 102.1 (C-8), 115.2 (C-6), 116.6 (C-10), 123.4 (C-1'), 127.3 (C-3), 128.7 (C-3', 5'), 128.7 (C-2', 6'), 129.1 (C-5), 137.0 (C-4'), 153.4 (C-2), 157.4 (C-9), 162.6 (C-7), 174.5 (C-4). MS (m/z) 253.4 $(M+H)^+$, 275.2 $(M+Na)^+$, 251.4 $(M-H)^-$. Anal. ($C_{16}H_{12}O_3$) for C, H. Cacld: 76.18, 4.79; found: 75.39, 4.82.

7-O-Ethoxycarbonylpentyl-4'-Methylisoflavone (Analog 30)

This compound was prepared by the same method as described for analog 5 except that starting materials were analog 29 and ethyl 6-bromohexanoate. The synthesis resulted in 900 mg of analog 30, a yield of 35.71% (w/w): mp 141-142° C. $^1$H NMR (DMSO-$d_6$) δ 1.16 (t, 3H, —$CH_3$), 1.44 (m, 2H, —$CH_2$—), 1.59 (m, 2H, —$CH_2$—), 1.76 (m, 2H, —$CH_2$—), 2.31 (m, 2H, —$CH_2$—), 2.33 (—$CH_3$), 4.04 (q, 2H, —$CH_2$—O—), 4.11 (t, 2H, —$CH_2$—O—), 7.06 (dd, IH, J=8.79, 2.53 Hz, 6-H), 7.14 (d, 1H, J=1.89 Hz, 8-H), 7.23 (d, 2H, J=8.04 Hz, 3', 5'-H), 7.47 (d, 2H, J=7.63 Hz, 2', 6'-H), 8.01 (d, 1H, J=8.86 Hz, 5-H), 8.42 (s, 1H, 2-H). $^{13}$C NMR (DMSO-$d_6$) δ 14.1 (—$CH_3$), 20.8 (—$CH_3$), 24.1 (—$CH_2$—), 24.9 ($CH_2$—), 28.0 (—$CH_2$—), 33.4 (—$CH_2$—), 59.6 (—$CH_2$—O—), 68.3 (—$CH_2$—O—), 101.0 (C-8), 115.0 (C-6), 117.5 (C-10), 123.6 (C-1'), 126.9 (C-3), 128.7 (C-2', 6'), 129.0 (C-5), 137.1 (C-4'), 153.7 (C-2), 157.4 (C-9), 163.1 (C-7), 172.8 (>C═O), 174.5 (C-4). Anal. ($C_{24}H_{26}O_5$) for C, H. Cacld: 73.08, 6.64; found: 73.11, 6.61.

7,4'-Dimethoxyisoflavone (Analog 31)

To a solution of 1.28 g of daidzin (5.0 mmol) in 40 ml of DMSO was added 3.84 g of NaOH pellets. The mixture was stirred at RT for 6 min and 3 ml of iodomethane (48.2 mmol) was added dropwise. The mixture was stirred at RT for another 6 min and poured into ice water. Product in the water was extracted with chloroform and dried. Residue was fractionated on a Sephadex LH-20 column (chloroform-methanol, 7:3). Fractions that contained pure product were pooled, concentrated, and recrystallized from acetone to give 450 mg of analog 31 (crystalline needles), a yield of 35.2 (w/w): mp 162-163° C. $^1$H NMR (DMSO-$d_6$) δ 3.79 (—$OCH_3$), 3.90 (—$OCH_3$), 6.99 (d, 2H, J=8.36 Hz, 3', 5'-H), 7.07 (dd, IH, J=8.88, 2.51 Hz, 6-H), 7.14 (d, 1H, J=1.82 Hz, 8-H), 7.52 (d, 2H, J=8.67 Hz, 2', 6'-H), 8.02 (d, 1H, J=8.88 Hz, 5-H), 8.40 (s, 1H, 2-H). Anal. ($C_{17}H_{14}O_4$) for C, H. Cacld: 72.33, 4.99; found:.72.47, 4.95.

7-Hydroxy-4'-Aminoisoflavone (Analog 32)

This compound was prepared by the reduction of analog 27. To a suspension of 500 mg of analog 27 and 50 ml of ethanol was added 1.0 g of zinc powder. The mixture was stirred at 50° C. while 10 ml of glacial acetic acid was added slowly through a span of 30 min. After analog 27 was completely reduced, reaction mixture was filtered and filtrate was concentrated. The concentrate was suspended in 20 ml of water and extracted with ethyl acetate. The organic layer was evaporated to dryness and residue was recrystallized from methanol:chloroform:petroleum ether (30-60° C.) (1:5:20) to give 153 mg of yellow amorphous powder of analog 32, a yield of 30.6% (w/w): mp 250° C. (decomposes). $^1$H NMR (DMSO-$d_6$) δ 6.59 (d, 2H, J=8.62 Hz, 3', 5'-H), 6.81 (d, 1H, J=2.63 Hz, 8-H), 6.89 (dd, 1H, J=8.93, 2.56 Hz, 6-H), 7.24 (d, 2H, J=8.08 Hz, 2', 6'-H), 7.94 (d, 1H, J=8.78 Hz, 5-H), 8.21 (s, 1H, 2-H). $^{13}$C NMR (DMSO-$d_6$) δ 102.1 (C-8), 113.4 (C-3', 5'), 115.2 (C-6), 117.5 (C-10), 119.0 (C-1'), 123.9 (C-3), 127.2 (-5), 129.5 (C-2', 6'), 148.5 (C-4'), 152.3 (C-2), 157.4 (C-9), 162.9 (C-7), 174.9 (C-4). MS (mz) 254.3 $(M+H)^+$, 276.2 $(M+Na)^+$, 252.6 $(M-H)^-$, Anal. ($C_{15}H_{10}O_3N$) for C, H, N. Cacld: 71.14, 4.38, 5.53; found: 70.89, 4.40, 5.49.

7-Ethoxycarbonylpentyl-4'-Aminoisoflavone (Analog 33)

This compound was prepared by reducing analog 28 under the same conditions described in analog 32. A total of 863 mg of analog 33 was obtained, a yield of 43.2% (w/w) mp 147-148° C. $^1$H NMR (DMSO-$d_6$) δ 1.17 (t, 3H, —$CH_3$), 1.44 (m, 2H, —$CH_2$—), 1.60 (—$CH_2$—), 1.74 (—$CH_2$—), 2.31 (—$CH_2$—), 4.04 (—$CH_2$—O—), 4.13 (—$CH_2$—O—), 6.60 (d, 2H, J=8.74 Hz, 3', 5'-H), 7.03 (dd, 1H, J=8.93, 2.56 Hz, 6-H), 7.09 (d, 1H, J=2.63 Hz, 8-H), 7.26 (d, 2H, J=6.52, 1.61 Hz, 2', 6'-H), 7.99 (d, 1H, J=8.88 Hz, 5-H), 8.29 (s, 1H, 2-H). $^{13}$C NMR (DMSO-$d_6$) δ 14.1 (—CH3), 24.2 (—$CH_2$—), 24.9 (—$CH_2$—), 28.0 (—$CH_2$—), 33.4 (—$CH_2$—), 59.7 (—$CH_2$—O—), 68.3 (—$CH_2$—O—), 100.8 (C-8), 113.4 (C-3', 5'), 114.8 (C-6), 117.5 (C-10), 118.8 (C-1'), 124.1 (C-3), 126.9 (C-5), 129.5 (C-2', 6'), 148.5 (C-4'), 152.3 (C-2), 157.3 (C-9), 162.9 (C-7), 174.9 (C-4). MS (m/z) 396.5 $(M+H)^{30}$ , 418.4 $(M+Na)^+$, 394.1 $(M-H)^-$. Anal. ($C_{23}H_{25}O_5N$) for C, H, N. Cacld: 69.86, 6.37, 3.54; found: 69.34, 6.29, 3.53.

7,8-Dimethoxyisoflavone (Analog 34)

This compound was prepared as described in the synthesis of analog 23. A mixture of 2.76 g of phenylacetic acid (20.08 mmol), 5.0 g of 2, 3-dimethoxylphenol (32.43 mmol) and 50 ml of boron trifluoride diethyl ether ate was stirred at 80° C. for 19 hours. Reaction mixture was then cooled to RT and washed with aqueous $K_2CO_3$ and water sequentially until pH of the filtrate approached neutrality. Product was extracted with ethyl acetate and concentrated to dryness. The residue, which contained mostly 2-hydroxy-3,4-dimethoxyphenylbenzylketone, was dissolved in 50 ml of 2-propanol and 3.0 ml of morpho line and 6.0 ml of triethyl orthoformate (36.07 mmol) were added. The mixture was stirred at 80° C. for 20 hours and evaporated to dryness. The residue was fractionated on a silica gel (chloroform-methanol system) and fractions that contained pure product were pooled, dried, and recrystallized from acetone to give 300 mg of analog 34 (crystalline plates), a yield of 6% (based on 2,3-dimethoxylphenol, w/w): mp 143-144° C. $^1$HNMR (DMSO-$d_6$) δ 3.89 (8-$OCH_3$), 3.96 (7-$OCH_3$), 7.30 (d, 1H, J=9.03, Hz, 6-H), 7.39 (t, 1H, J=6.94 Hz, 4'-H), 7.43 (t, 2H, J=7.06, 7.72 Hz, 3', 5'-H), 7.57 (dd, 2H, J=7.26, 1.44 Hz, 2', 6'-H), 7.87 (d, 1H, J=8.88 Hz, 5-H), 8.50 (s, 1H, 2H). $^{13}$C NMR (DMSO-$d_6$) δ 56.5 (—$OCH_3$), 60.9 (—$OCH_3$), 111.0 (C-6), 118.5 (C-10), 120.9 (C-3), 123.3 (C-1'), 127.8 (C-5), 128.1 (C-3', 5'), 128.9 (C-2', 6'), 131.9 (C-4'), 136.1(C-8), 149.9(C-7), 154.1 (C-2), 156.2 (C-9), 174.6 (C-4). MS (m/z) 283.3 $(M+H)^+$, 305.4 $(M+Na)^+$, 281.9 $(M-H)^-$. Anal. ($C_{17}H_{14}O_4$) for C, H. Cacld: 72.33, 4.99; found: 72.21, 4.97.

7-Ethylisoflavone (Analog 35)

This compound was prepared by the same method described for the synthesis of analog 23. To a solution of 6.51 g of phenylacetic acid (47.81 mmol) in 50 ml of boron trifluroide diethyl etherate was added 6.5 ml of 3-ethylphenol (53.20 mmol). The mixture was stirred at 80° C. for 21 hours, cooled to RT, and then washed with aqueous $K_2CO_3$ and water until the pH of wash approached neutrality. The product was extracted with ethyl acetate and concentrated. Residue was dissolved in 50 ml of 2-propanol and 8 ml of triethyl formate (48.1 mmol) and 3 ml of morpho line were added. The mixture was stirred at 80° C. for 7 hours and solvent was removed by flash evaporation. The syrup obtained was dissolved in 30 ml of methanol, stirred at 50° C. for 30 min, cooled to room temperature, and kept at 4° C. overnight. Crystals were collected by filtration and washed with small portions of acetone to give 790 mg of analog 35, a yield of 12.2% (based on 3-ethylphenol, w/w): mp 103-104° C. $^1$H NMR (DMSO-$d_6$) δ 1.35 (t, 3H, —$CH_3$), 2.78 (q, 2H, —$CH_2$—), 7.38 (m, 4'-H), 7.39 (dd, 1H, J=8.10, 1.91 Hz, 6-H), 7.44 (t, 2H, J=7.77 Hz, 3', 5'-H), 7.52 (d, 1H, J=2.0 Hz, 8H), 7.59 (dd, 2H, J=7.35, 1.38 Hz, 2', 6'-H), 8.05 (d, 1H, J=8.54 Hz, 5-H), 8.51 (s, 1H, 2-H). $^{13}$C NMR (DMSO-$d_6$) δ 14.9 (—$CH_3$), 28.2 ($CH_2$—), 116.7 (C-6, 8), 121.8 (C-10), 123.8 (C-3), 125.4 (C-1'), 125.8 (C-7), 127.8 (C-5), 128.1 (C-3', 5'), 128.9 (C-2', 6'), 131.9 (C-4'), 154.4 (C-2), 155.9 (C-9), 174.9 (C-4). MS (m/z), 251.4 $(M+H)^+$, 273.2 $(M+Na)^+$, 249.3 $(M-H)^-$. Anal. ($C_{17}H_{14}O_2$) for C, H. Cacld: 81.58, 6.91; found: 80.92, 6.87.

7-Ethoxylcarbonylpentoxypuerarin (Analog 36)

This compound was prepared by the same method described for analog 5. To a solution of 3.5 g of puerarin (8.41 mmol) in 60 ml of DMF, 2.76 g of anhydrous $K_2CO_3$ (20.0 mmol) and 6.0 ml of ethyl 6-bromohexanoate (33.6 mmol) were added. The mixture was stirred at 80° C. for 6 hours, poured into ice water, and extracted with ethyl acetate. Solvent was evaporated and residue was fractionated on a on Silica gel column (chloroform:methanol, 8:2) followed by a Sephadex LH-20 column (chloroform:methanol, 7:3). Final product was recrystallized from petroleum ether:chloroform:methanol (10:0.5:0.1) to give 3.19 g of analog 36 (white amorphous powder), a yield of 91.14% (w/w): mp 165-168° C. $^1$H NMR (DMSO-$d_6$) δ 1.18 (—$CH_3$), 1.47 (—$CH_2$—), 1.58 (—$CH_2$—), 1.77 (—$CH_2$—), 2.32 (—$CH_2$—), 4.07 (—$CH_2$—O—), 4.12 (—$CH_2$—O—), 3.08-5.23 (m, H from glucose), 6.81 (dd, 2H, J=7.29, 2.11 Hz, 3', 5H), 7.22 (d, IH, J=8.57, 6-H), 7.41 (dd, 2H, J=8.6, 2.1 Hz, 2', 6'-H), 8.08 (d, 1H, J=9.0 Hz, 5-H), 8.41 (s, 1H, 2-H), 9.53 (s, 1H, 4'-OH). $^{13}$C NMR (DMSO-$d_6$) δ 14.1 (—$CH_3$), 24.1 (—$CH_2$—), 25.0 (—$CH_2$'), 28.3 (—$CH_2$—), 33.5 (—$CH_2$—), 59.7 (—$CH_2$—O—), 61.7 (C-6"), 68.4 (—$CH_2$—O—), 70.2 (C-4"), 70.6 (C-2"), 73.0 (C-1"), 78.8 (C-3"), 81.8 (C-5"), 111.3 (C-8), 114.8 (C-6), 114.9 (C-3', 5'), 117.2 (C-10), 122.4 (C-1'), 123.1 (C-3), 126.8 (C-5), 130.0 (C-2', 6'), 155.1 (C2), 157.1 (C-9), 157.4 (C-4'), 162.1 (C-7), 172.9 (—C═O), 175.0 (C-4). MS (m/z) 559.6 $(M+H)^+$, 581.5 $(M+Na)^+$, 557.9 $(M-H)^-$. Anal. ($C_{29}H_{34}O_{11}$) for C, H. Cacld: 62.36, 6.14; found: 61.92, 6.17.

Daidzein 7-ω-Hydroxyhexyl Ether (Analog 50)

Analog 50 was synthesized according to the method described for analog 75 using 6-bromo-1-hexanol (3 ml, 22.93 mmol) as the alkylating agent. After reflux, the reaction mixture was refrigerated for 12 hours. Precipitates formed during refrigeration were collected and fractionated on a Sephadex LH-20 column in methanol. Fractions that contained pure product were pooled, dried and recrystallized from acetone to give 1.16 g of analog 50. Analyses: white amorphous powder; yield 16.4%; mp 177-178.5° C.; $^1H$ NMR (DMSO-$d_6$) δ 1.35 (m, 2H, —$CH_2$—), 1.43 (m, 4H, —$CH_2$—$CH_2$—), 1.75 (m, 2H, —$CH_2$—), 3.40 (m, 2H, —$CH_2$—), 4.1 (t, —$CH_2$—O—), 6.81 (dd, 2H, J=8.7 Hz, 1.6 Hz, H-3', H-5'), 7.04 (dd, 1H, J=8.86 Hz, 1.98 Hz, H-6), 7.10 (d, 1H, J=1.99, H-8), 7.40 (dd, 2H, J=8.7 Hz, 1.58 Hz, H-2', H-6'), 8.0 (d, 1H, J=8.86 Hz, H-5), 8.34 (s, IH, H-2), 9.53 (s, 1H, OH-4'); $^{13}C$ NMR δ 25.2 (—$CH_2$—), 25.3 (—$CH_2$—), 28.5 (—$CH_2$—), 32.5 (—$CH_2$—), 60.6 (—$CH_2$—O—), 68.4 (—O—$CH_2$—), 100.9 (C-8), 114.9 (C-6), 114.9 (C-3', C-5'), 117.5 (C-10), 122.4 (C-1'), 123.7 (C-3), 126.9 (C-5), 130.1 (C-2', C-6'), 153.1 (C-2), 157.2 (C-9), 157.4 (C-4'), 163.0 (C7), 174.7 (C-4); MS m/z 355.3 $(M+H)^+$. Elementary analysis ($C_{21}H_{22}O_5$). Cacld: C, 71.17; H, 6.26. Found: C, 70.82, H, 6.44.

Daidzein 7-ω-Ethoxycarbonylbutyl Ether (Analog 53)

To a solution of 5.1 g of daidzein (20.08 mmol), 8.0 mL of 2 N aq. KOH (16 mmol) and 50 mL of acetone was added 3.5 mL of ethyl-5-bromovalerate (22.1 mmol). The mixture was refluxed with gentle stirring for 72 hours and cooled and kept at 4° C. overnight. Precipitates were collected on a fritted funnel and fractionated on a Sephadex LH-20 column in chloroform:methanol (7:3). Fractions that contained pure product were pooled, dried and recrystallized from acetone to give 670 mg of analog 53. Analyses: colorless crystalline plates; yield 8.8%; mp 146-148° C.; $^1H$ NMR (DMSO-$d_6$) δ 1.17 [t, 3H, —$CH_3$], 1.69 (m, 2H, —$CH_2$—), 1.77(m, 2H, —$CH_2$—), 2.38 (t, 2H, —$CH_2$—), 4.05 (m, 2H, $CH_2$—O—), 4.12 (m, 2H, —$CH_2$—O—), 6.81 (dd, 2H, J=8.67 Hz, 1.5 Hz, H-3', H-5'), 7.04 (dd, 1H, J=8.89 Hz, 2.1 Hz, H-6), 7.11 (d, 1H, J=2.1 Hz, H-8), 7.39 (dd, 2H, J=8.7 Hz, 1.5 Hz, H-2', H-6'), 8.0 (d, IH, J=8.89 Hz, H-5), 8.35 (s, 1H, H-2), 9.55 (s, 1H, OH-4'); $^{13}C$ NMR δ 14.1 (—$CH_3$), 21.1 (—$CH_2$—), 27.7 (—$CH_2$—), 59.7 (—$CH_2$—O—), 68.1 (—$CH_2$—O—), 100.9 (C-8), 114.9 (C-6), 114.9 (C-3', C-5'), 117.5 (C-10), 122.4 (C-1'), 123.7 (C-3), 126.9 (C-5), 130.1 (C-2', C-6'), 153.1 (C-2), 157.3 (C-9), 157.4 (C-4'), 162.9 (C-7), 172.7 (O═C—O—), 174.7 (C-4). MS m/z 383.3 $(M+1)^+$. Elementary analysis ($C_{22}H_{22}O_6$). Cacld: C, 69.09; H, 5.80. Found: C, 68.60; H, 5.84.

Daidzein 7-ω-Hydroxynonyl Ether (Analog 57)

To a suspension of 5.1 g of daidzein (20.08 mmol) in 60 ml of acetone was added 15 ml of 2 N aq. KOH (30 mmol). The mixture was stirred at room temperature until daidzein was completely dissolved. Five g of 9-bromo-1-nonanol (22.41 mmol) was then added and the mixture was stirred under gentle reflux for 72 hours. Reaction mixture was cooled and kept at 4° C. overnight. Precipitates were collected by filtration and were fractionated on a Sephadex LH-20 column in chloroform:methanol (7:3). Fractions that contained pure product were pooled, concentrated and recrystallized from acetone to yield 305 mg of analog 57. Analyses: colorless crystalline plates; yield 5.98%; mp 165-167° C.; $^1H$ NMR (DMSO-$d_6$) δ 1.27 [m, 8H, (—$CH_2$—$)_4$], 1.40 (m, 4H, —$CH_2$—$CH_2$—), 1.73 (m, 2H, —$CH_2$—), 3.37 (m, 2H, —$CH_2$—), 4.09 (t, —$CH_2$—O—), 6.81 (d, 2H, J=8.75 Hz, 1.58 Hz, H-3', H-5'), 7.04 (dd, 1H, J=8.87 Hz, 2.1 Hz, H-6), 7.10 (d, 1H, J=2.1 Hz, H-8), 7.39 (d, 2H, J=8.75 Hz, 1.58 Hz, H-2', H-6'), 8.0 (d, IH, J=8.86 Hz, H-5), 8.34 (s, 1H, H-2), 9.53 (s, 1H, OH-4'); $^{13}C$ NMR δ25.4 (—$CH_2$—), 25.5 (—$CH_2$—), 28.4 (—$CH_2$—), 28.7 (—$CH_2$—), 28.9 (—$CH_2$—), 29.0 (—$CH_2$—), 32.5 (—$CH_2$—), 60.7(—$CH_2$—O—), 68.4 (—O—$CH_2$—), 100.9 (C-8), 114.9 (C-6), 114.9 (C-3', C-5'), 117.5 (C-10), 122.4 (C-1'), 123.7 (C-3), 126.9 (C-5), 130.0 (C2', C-6'), 153.0 (C-2), 157.2 (C-9), 157.4 (C-4'), 163.0 (C-7), 174.7 (C-4); MS m/z 397.5 $(M+H)^+$, 419.4 $(M+Na)^+$, 435.4 $(M+K)^+$, 395.3 $(M-H)^-$. Elementary analyses ($C_{24}H_{28}O_5$). Cacld: C, 72.71, H, 7.12. Found: C, 73.11; H, 7.13.

Daidzein 7-ω-Hydroxydodecyl Ether (Analog 63)

Analog 63 was synthesized and purified according to the procedures described for analog 57 using 12-bromo-1-dodecanol (5 g, 18.85 mmol) as the alkylating agent. Analyses: white amorphous powder; yield 20.5%; mp 142-144° C.; $^1H$ NMR (DMSO-$d_6$) δ 1.23 [m, 14H, (—$CH_2$—$)_7$], 1.37 (m, 4H, —$CH_2$—$CH_2$—), 1.73 (m, 2H, —$CH_2$—), 3.36 (m, 2H, $CH_2$—O—), 4.08 (t, —$CH_2$—O—), 6.81 (dd, 2H, J=8.69 Hz, 1.58 Hz, H-3', H-5'), 7.04 (dd, 1H, J=8.86 Hz, 1.9 Hz, H-6), 7.09 (d, IH, J=1.9 Hz, H-8), 7.40 (dd, 2H, J=8.69 Hz, 1.58 Hz, H-2', H-6'), 7.98 (d, 1H, J=8.86 Hz, H-5), 8.34 (s, 1H, H-2), 9.55 (s, 1H, OH-4'); $^{13}C$ NMR δ 25.4 [(—$CH_2$—$)_2$], 25.5 (—$CH_2$—), 28.4 (—$CH_2$—), 28.7 (—$CH_2$—), 28.9 (—$CH_2$—), 29.1 (—$CH_2$—), 32.5 (—$CH_2$—), 60.7 (—$CH_2$—O—), 68.4 (—O—$CH_2$—), 100.9 (C-8), 114.8 (C-6), 114.8 (C3', C-5'), 117.5 (C-10), 122.4 (C-1'), 123.7 (C-3), 126.9 (C-5), 130.0 (C-2', C-6'), 153.0 (C-2), 157.2 (C-9), 157.4 (C-4'), 163.0 (C-7), 174.7 (C-4); MS m/z 439.6 $(M+H)^+$. Elementary analysis ($C_{27}H_{34}O_5$). Cacld: C, 73.95; H, 7.81. Found: C, 74.20; H, 7.61.

Daidzein 7-(1"H-indole-3"-yl)-Ethyl Ether (Analog 73)

To a solution of 5.1 g of daidzein (20.08 mmol) in 60 ml of DMF was added 7.7 g of $K_2CO_3$ (55.71 mmol) and 5.0 g of 3-(2-bromoethyl)indole (22.31 mmol) successively. The mixture was stirred and heated at 80° C. for 4 hours and precipitated by pouring reaction mixture into 200 ml of ice water. Precipitates were collected by filtration and fractionated on a Sephadex-LH-20 column in chloroform:methanol (7:3). Fractions that contained pure product were pooled, concentrated and recrystallized from acetone to give 2.5 g of analog 73. Analyses: white crystalline product; yield, 49%; mp 203-205° C. $^1H$ NMR (DMSO-$d_6$) δ 4.35 (t, 2H, —O—$CH_2$—), 6.84 (d, 2H, J=8.7 Hz, H-3', 5'), 7.01 (dd, 1H, J=7.4 Hz, H-7"), 7.05 (dd, 1H, J=8.9, 2.6 Hz, H-6), 7.10 (dd, 1H, J=8.2, 2.1, H5"), 7.29 (d, 1H, J=1.8 Hz, H-8), 7.38 (d, 1H, J=8.0 Hz, H-4"), 7.41 (d, 2H, J=8.7 Hz, H-2', 6'), 7.62 (d, 1H, J=7.9 Hz, H-6"), 7.95 (s, 1H, H-2"), 8.01 (d, 1H, J=8.9 Hz, H-5), 8.32 (s, 1H, H-2), 9.54 (s, 1H, OH-4'). $^{13}C$ NMR (DMSO-$d_6$) δ 24.7 (—$CH_2$—), 68.9 (—$CH_2$—O—), 101.0 (C-8), 110.2 (C-7"), 111.4 (C-5"), 114.9 (C-3', 5'), 115.0 (C-6), 117.6 (C-10), 118.4 (C-3"), 121.0 (C-8"), 122.4 (C-1"), 123.3 (C-4"), 123.7 (C-3), 127.3 (C-5), 130.1 (C-2', 6'), 136.2 (C-2"), 153.0 (C-2), 153.0 (C-9"), 157.3 (C-9); 157.4 (C-4'), 162.9 (C-7), 174.4 (C-4). MS (m/z) 397.9 $(M)^+$. Elementary analyses ($C_{25}H_{19O_4}N$) for C, H, N: Cacld. 75.55, 4.82, 3.52; found 72.02, 5.60, 6.08.

Daidzein 7-Hydroxyethyl Ether (Analog 75)

To a suspension of 5.3 g of daidzein (20.87 mmol) in 60 ml of acetone was added with vigorous stirring 13 ml of 2 N aq. KOH (26 mmol). After daidzein was completely dissolved, 2 ml of 2-bromoethanol (28.21 mmol) was added and the reaction mixture was refluxed with gentle stirring for 72 hours. Volatile solvent was evaporated and residue was partitioned in water and ethyl acetate. Product in the ethyl acetate layer was further purified by a silica gel column in petroleum ether:ethyl acetate:methanol (6:3:1) followed by a Sephadex LH-20 column in methanol. Fractions that contained pure product were pooled, dried and recrystallized from acetone to give 1.7 g of analog 75. Analyses: white amorphous powder; yield 28.5%; mp 210-212° C.; MS m/z 299.1 $(M+H)^+$. Elementary analysis ($C_{17}H_{14}O_5$): Cacld: C, 68.45; H, 4.73. Found: C, 67.86; H, 4.23.

Daidzein 7-[2,4-(1H, 3H)-quinazolinedione-3-N-yl]-ethoxyl ether (Analog 78)

To the suspension of daidzein (5.0 g, 20.06 mmol) and 50 ml of acetone was added 30 ml of 2N aq. KOH (60.0 mmol) and 5.0 g of 3-(2-chloroethyl)-2,4 (1H, 3H) quinazolinedione (22.26 mmol). The mixture was stirred at room temperature for 48 h. Precipitates were filtered, dried and fractionated first on a silica gel column (chloroform-methanol, 9.25:0.75) followed by a Sephadex-LH-20 column (chloroform-methanol, 7:3). Fractions containing pure product were pooled, concentrated and recrystallized from acetone to yield 617 mg HPLC-pure product. Analyses: white crystals; yield, 12.9%; mp 270° C. (decompose). $^1$HNMR (DMSO-$d_6$) δ, 4.33-4.38 (m, 4H, —N—$CH_2$—$CH_2$—O—), 6.82 (dd, 2H, J=8.65, 3.2 Hz, 3', 5'-H), 7.03 (dd, 1H, J=9.01, 2.44 Hz, 6-H), 7.18 (d, 1H, J=7.27 Hz, 7"-H), 7.19 (d, 1H, 8-H), 7.21 (d, 1H, J=7.72 Hz, 8"-H), 7.38 (d, 2H, J=8.55 Hz, 2', 6'-H), 7.66 (t, 1H, J=7.43, 1.36, 9"-H), 7.94 (d, 1H, J=7.75, 6"-H), 7.99 (d, 1H, J=9.0 Hz, 5-H), 8.35 (s, 1H, 2-H). 9.58 (4'-OH). $^{13}$CNMR (DMSO-$d_6$) δ,38.5 (—N—$CH_2$—), 65.0 (—$CH_2$—O—), 101.1 (C-8), 113.7(C-9"), 115.0(C-7"), 115.0 (C-3', 5'), 115.2(C-6), 117.8 (C-10), 122.3 (C-5"), 122.6 (C-1'), 123.7 (C-3), 127.0 (C-6"), 127.4 (C-5), 130.1 (C-2', 6'), 135.1 (C-8"), 139.5 (C-10"), 150.1 (C-2"), 153.1 (C-2), 157.3 (C-9), 157.3 (C-4'), 162.1 (C-4"), 162.5 (C-7), 174.7 (C-4). Anal. ($C_{25}H_{18}O_6N_2$) for C, H, N. Cacld, 67.87, 4.10, 6.33; found, 64.60, 4.13, 6.40.

Daidzein 7-(4", 6"-dimethoxy-1", 3", 5"-triazine)-2"-yl Ether (Analog 81) and daidzein 7,4'-di-(4", 6"-dimethoxy-1", 3", 5"-triazine)-2"-yl Ether (Analog 82)

To a solution of 5.1 g of daidzein (20.08 mmol) in 60 ml of DMF was added 3.2 g of $K_2CO_3$ (23.1 mmol) and 5.0 g of 2-chloro-4,6-dimethoxy-1,3,5-triazine (28.5 mmol) successively. The mixture was stirred and heated at 80° C. for 4 hours and products were precipitated in 200 ml of ice water. Precipitates were collected by filtration and fractionated on a Sephadex-LH-20 column in chloroform: methanol (7:3). Fractions that contained pure products were pooled accordingly and concentrated and recrystallized from acetone to give 1.29 g analog 81 and 7.5 g analog 82. Analyses: analog 81, white crystals; yield, 25.3%; mp 226-228° C. $^1$H NMR (DMSO-$d_6$) δ 3.91 (s, 6H, 2X-$OCH_3$), 6.82 (dd, 2H, J=8.7, 1.7 Hz, H-3', 5'), 7.41 (dd, 1H, J=8.8, 1.8 Hz, H-6), 7.42 (d, 2H, J=8.8, 1.8 Hz, H-2', 6'), 7.69 (d, 1H, J=1.96 Hz, H-8), 8.18 (d, 1H, J=8.8 Hz, H-5), 8.45 (s, 1H, H-2), 9.58 (s, 1H, OH-4'). $^{13}$C NMR (DMSO-$d_6$) 055.3 (—$OCH_3$), 55.4 (—$OCH_3$), 111.2 (C-8), 115.0 (C-3', 5'), 119.9 (C-10), 121.3 (C-6), 121.7(C-8), 122.0 (C-1'), 124.0 (C-3), 127.0 (C-5), 130.1 (C-2', 6'), 153.8 (C-2), 155.3 (C-6"), 156.1 (C-4"), 157.4 (C-9), 157.5 (C-4'), 172.2 (C-7), 173.3(C-2"), 174.8 (C-4). MS (m/z) 394.3 $(M+H)^+$, 416.6 $(M+Na)^+$, 432.4 $(M+K)^+$. Elementary analyses ($C_{20}H_{15}O_6N_3$) for C, H, N: Cacld. 61.07, 3.84, 10.68; found 60.90, 4.06, 10.76. Analog 82, white amorphous powder; yield, 70.2%; mp 265° C. (decompose). $^1$H NMR, $^{13}$C NMR and MS similar to analog 81. Elementary analyses ($C_{25}H_{20}O_8N_6$) for C, H, N: Cacld. 56.39, 3.79, 15.78; found 57.06, 3.99, 15.71.

Daidzein 7-N-(2"(3"H)-Benzothiazolonyl)-Methyl Ether (Analog 83)

To a solution of 5.1 g of daidzein (20.08 mmol) in 60 ml of DMF was added 3.0 g of $K_2CO_3$ (21.7 mmol) and 5.0 g of 3-chloromethyl-2(3H)-benzothiazolone (25.0 mmol) successively. The mixture was stirred and heated at 80° C. for 14 hours and products were precipitated in 200 ml of ice water. Precipitates were collected by filtration and fractionated on a Sephadex-LH-20 column in chloroform:methanol (7:3). Fractions that contained pure product were pooled, concentrated and recrystallized from acetone to give 5.02 g of analog 83. Analyses: colorless crystals; yield, 98.4%; mp 234-235° C. $^1$H NMR (DMSO-$d_6$) δ 6.1 (s, 2H, —O—$CH_2$—), 6.82 (d, 2H, J=8.7, 2.5 Hz, H-3', 5'), 7.15 (dd, 1H, J=8.9, 1.9 Hz, H-6), 7.27 (t, 1H, J=7.34, 7.75 Hz, H-7"), 7.41 (d, 2H, J=8.7 Hz, H-2', 6'), 7.42 (d, 1H, J=8.8 Hz, H-4"), 7.43 (d, 1H, J=2.7 Hz, H-8), 7.50 (d, 1H, J=8.2 Hz, H-5"), 7.70 (d, 1H, J=7.82 Hz, H-6"), 8.04 (d, 1H, J=8.9 Hz, H-5), 8.39 (s, 1H, H-2). $^{13}$C NMR (DMSO-$d_6$) δ 69.5 (—$CH_2$—O—), 102.6 (C-8), 112.0 (C-1"), 115.0 (C-3', 5'),115.3 (C-6), 118.6 (C-10), 121.1 (C-4"), 122.2 (C-1'), 123.1 (C-5"), 123.8 (C-3), 124.2 (C-6"), 126.9 (C-9"), 127.3 (C-5), 130.1 (C-2', 6'), 135.6 (C-8"), 153.3 (C-2), 157.0 (C-9), 157.3 (C-4'), 160.0 (C-7), 169.6 (—S—C═O),174.4 (C-4). MS (m/z) 440.4 $(M+Na)^+$, 416.8 $(M-H)^-$. Elementary analyses ($C_{23}H_{15}O_5NS$) for C, H, N, S: Cacld.66.18, 3.62, 3.36, 7.68; found 65.80, 3.6, 3.42, 7.52.

Daidzein 4'-(1"-Phenyl-1"H-Tetrazole-5"-yl) Ether (Analog 86)

To a solution of 5.1 g of daidzein (20.08 mmol) in 60 ml of DMF was added 3.0 g of $K_2CO_3$ (21.74 mmol) and 3.6 g of 5-chloro-1-phenyl-1H-tetrazole (20.0 mmol) successively. The mixture was stirred and heated at 80° C. for 4 hours and products were precipitated in 200 ml of ice water. Precipitates were collected by filtration and fractionated on a Sephadex-LH-20 column in chloroform:methanol (7:3). Fractions that contained pure product were pooled, concentrated and recrystallized from acetone to give 4.4 g of analog 86. Analyses: colorless crystals; yield, 86.3%; mp 265-267° C. $^1$H NMR (DMSO-$d_6$) δ 6.89 (d, 1H, J=2.2 Hz, H-8), 6.96 (d, 2H, J=8.8, 2.1 Hz, H-6), 7.58 (dd, 2H, J=9.31, 1.64 Hz, H-6", 10"), 7.61 (d, 1H, J=7.4 Hz, H-8"), 7.67 (dd, 2H, J=7.8, H 7", 9"), 7.70 (dd, 2H, J=8.7, 1.6 Hz, H-3', 5'), 7.87 (d, 2H, J=7.83 Hz, H-2', 6'), 7.99 (d, 1H, J=8.8 Hz, H-5), 8.47 (s, 1H, H-2), 10.8 (s, 1H, OH-7). —C NMR (DMSO-$d_6$) δ 102.2 (C-8), 115.4 (C-6), 116.5 (C-10), 119.7 (C-1'), 122.5 (C-3), 123.2 (C-2', 6'), 127.3 (C-5), 129.9 (C-3', 5'), 129.9 (C-6", 10"), 130.4 (C-8"), 130.5 (C-7", 9"), 132.6 (C-11"), 152.9 (C-2), 154.1 (C-5"), 157.5 (C-9), 159.6 (C-4'), 162.8 (C-7), 174.3 (C-4). MS (m/z) 421.3 $(M+Na)^+$, 437.2

$(M+K)^+$, 397.2 $(M-H)^-$. Elementary analyses ($C_{22}H_{14}O_4N_4$) for C, H, N. Cacld. 66.32, 3.54, 14.06; found 65.67, 3.62, 14.12.

Daidzein 7-(6"-Chloropiperonyl) Ether (Analog 87)

To a solution of 5.1 g of daidzein (20.08 mmol) in 60 ml of DMF was added 2.7 g of $K_2CO_3$ (19.6 mmol) and 5.0 g of 6-chloropiperonylchloride (24.4 mmol) successively. The mixture was stirred and heated at 80° C. for 15 hours and products were precipitated in 200 ml of ice water. Precipitates were collected by filtration and fractionated on a Sephadex-LH-20 column in chloroform:methanol (7:3). Fractions that contained pure product were pooled, concentrated and recrystallized from acetone to give 6.4 g of analog 87. Analyses: colorless crystals; yield, 75.5%; mp 254-256° C. $^1$H NMR (DMSO-$d_6$) δ 5.18 (—O—$CH_2$—), 6.10(s, 2H, —O—$CH_2$—O—), 6.81 (d, 2H, J=8.6,1.6 Hz, H-3', 5'), 7.13 (dd, 1H, J=8.9, 2.6 Hz, H-6), 7.16 (s, 1H, H-5"), 7.23 (s, 1H, H-2"), 7.27 (d, 1H, J=2.0 Hz, H-8), 7.40 (d, 2H, J=8.7 Hz, H-2', 6'), 8.03 (d, 1H, J=8.9 Hz, H-5), 8.37 (s, 1H, H-2), 9.47 (s, 1H, 4'-OH). $^{13}$C NMR (DMSO-$d_6$) δ 67.7 (—$CH_2$—O—), 101.5 (C-8), 102.3 (—O—$CH_2$—O—), 109.8 (C-2"), 110.3 (C-5"), 115.0 (C-3', 5'), 115.0 (C-6), 117.9 (C-10), 122.3 (C-1'), 123.7 (C-3), 125.4 (C-1"), 127.0 (C-5), 130.0 (C-2', 6'), 146.7 (C-3"), 148.4 (C4"), 153.2 (C-2), 153.2 (C-2"), 157.2 (C-9), 157.3 (C-4'), 162.4 (C-7), 174.4 (C-4). MS (m/z) 423.2 $(M+H)^+$, 445.3 $(M+Na)^+$, 461.3 $(M+K)^+$. Elementary analyses ($C_{23}H_{15}O_6Cl$): Cacld C, 65.34; H, 3.58. Found: C, 64.31; H, 3.61.

Daidzein 7-ω-(3"-Chlorophenylpiperozine)-4-N-Propyl Ether (Analog 88)

To a solution of 5.1 g of daidzein (20.08 mmol) in 60 ml of DMF was added 3.0 g of $K_2CO_3$ (21.74 mmol) and 6.2 g of 1-(3-chlorophenyl)-4-(3-chloropropyl) piperazine monohydrochloride (20.02 mmol) successively. The mixture was stirred and heated at 80° C. for 4 hours and products were precipitated in 200 ml of ice water. Precipitates were collected by filtration and fractionated on a Sephadex-LH-20 column in chloroform: methanol (7:3). Fractions that contained pure product were pooled, concentrated and recrystallized from acetone to give 3.48 g of analog 88. Analyses: pure white amorphous powder; yield, 68.2%; mp 183-185 ° C. $^1$H NMR (DMSO-$d_6$) δ 1.94 (—$CH_2$—), 2.48 (—$CH_2$N—), 2.50 (H-b, d), 3.15 (H-a, c), 4.16 (—O—CH2-), 6.76 (dd, 1H, J=7.81, 1.4 Hz, H-4"), 6.83 (d, 2H, J=8.6, 1.6 Hz, H-3', 5"),6.87 (dd, 1H, J=8.5, 2.0 Hz, H-6"), 6.91 (d, IH, J=1.85 Hz, H-2"), 7.05 (dd, 1H, J=8.9, 1.97 Hz, H-6), 7.11 (d, 1H, J=2.5 Hz, H-8), 7.19 (t, 1H, J=8.4 Hz, H-5"), 7.39 (d, 2H, J=8.7, 1.6 Hz, H-2', 6'), 8.01 (d, 1H, J=8.9 Hz, H-5), 8.34 (s, 1H, H-2), 9.55 (s, 1H, OH-4'). $^{13}$C NMR (DMSO-$d_6$) 025.9 (—$CH_2$—), 47.6 (C-b, d), 52.6 (C-c), 54.2 (C-a), 66.8 (—$CH_2$—O—), 101.0 (C-8), 113.6 (C-2"), 114.4 (C-6"), 114.9 (C-6), 115.0 (C-3', 5'), 117.5 (C-10), 117.9 (C-4"), 122.4 (C-1'), 123.7 (C-3),126.9 (C-5), 130.1 (C-2', 6'),130.4 (C-5"), 133.8 (C-1"), 152.2 (C-3"), 153.1 (C-2), 157.2 (C-9), 157.4 (C-4'), 163.0 (C-7), 174.4 (C-4). MS (m/z) 491.3 $(M+H)^+$. Elementary analyses ($C_{28}H_{27}O_4N_2Cl$): Cacld. C, 68.5; H, 5.54. Found: C, 65.63; H, 5.54.

Daidzein 7-(2"-Ethoxycarbonylfurfuryl) Ether (Analog 89)

To a solution of 5.1 g of daidzein (20.08 mmol) in 60 ml of DMF was added 2.95 g of $K_2CO_3$ (21.38 mmol) and 5.0 g of ethyl5-(chloromethyl)-2-furancarboxylate (26.51 mmol) successively. The mixture was stirred and heated at 80° C. for 1.5 hours and products were precipitated in 200 ml of ice water. Precipitates were collected by filtration and fractionated on a Sephadex-LH-20 column in chloroform: methanol (7:3). Fractions that contained pure product were pooled, concentrated and recrystallized from acetone to give 5.89 g of analog 89. Analyses: white amorphous powder; yield, 72.3%; mp 208-210° C. $^1$H NMR (DMSO-$d_6$) δ 1.27 (—$CH_3$), 4.28 (—$CH_2$—O—), 5.34 (—O—$CH_2$—), 6.81 (d, 2H, J=8.7, 1.68 Hz, H-3', 5'), 6.87 (d, 1H, J=3.2 Hz, H-8), 7.15 (dd, 1H, J=8.9, 2.7 Hz, H-6), 7.31 (d, 1H, J=7.5 Hz, H-4"), 7.32 (d, 1H, J=6.8 Hz, H-3"), 7.40 (dd, 2H, J=8.2, 1.8 Hz, H-2', 6'), 8.03 (d, 1H, J=8.9 Hz, H-5), 8.38 (s, 1H, H-2), 9.55 (s, 1H, OH-4'). $^{13}$C NMR (DMSO-$d_6$) δ 14.1 (—$CH_3$), 60.8 (—$CH_2$—O—), 62.1 (—$CH_2$—O—), 101.6 (C8), 113.1 (C-4"), 115.0 (C-6), 115.0 (C-3', 5'), 118.1 (C-10), 118.9 (C-3"), 122.3 (C-1'), 123.8 (C-3), 127.1 (C-5), 130.1 (C-2', 6'), 144.4 (C-2"), 153.2 (C-5"), 153.4 (C-2), 157.2 (C-9), 157.3 (C-4'), 157.8 (—C═O), 161.9 (C-7), 174.8 (C-4). MS (m/z) 407.5 $(M+H)^+$, 429.4 $(M+Na)^+$, 445.4 $(M+K)^+$. Elementary analyses ($C_{23}H_{18}O_7$) for C, H: Cacld. 67.98, 4.46; found 67.30, 4.62.

Daidzein 7-(1,8-naphthalimide-N-yl)-ethoxyl ether Analog (90)

Daidzein (5.1 g, 20.06 mmol) was dissolved in 60 ml of DMF, and 3.0 g of $K_2CO_3$ (21.74 mmol) and 5.0 g of 1-(chloromethyl)-1H-benzotriazole (19.25 mmol) were added successively. The mixture was stirred at 80° C. for 4 h and then poured into 200 ml ice water. Precipitates were collected, dried, and purified on Sephadex-LH-20 column (chloroform:methanol/7:3). Fractions containing product were pooled, concentrated and recrystallized from acetone to give 562 mg crystalline product. Analyses: yield, 11.0% w/w; mp 278-280° C. $^1$HNMR (DMSO-$d_6$) δ, 4.42 (t, 2H, —N—$CH_2$—), 4.49 (t, 2H, —$CH_2$—O—), 6.82 (dd, 2H, J=8.73, 2.57 Hz, 3', 5'-H), 7.01(dd, 1H, J=8.86, 2.57 Hz, 6-H), 7.18 (d, 1H, J=1.98 Hz, 8-H), 7.37 (dd, 2H, J=6.4, 1.71 Hz, 2', 6'-H), 7.85 (t, 2H, J=8.01, 7.60 Hz, 3", 6"-H), 7.95 (d, 1H, J=8.91 Hz, 5-H), 8.32 (s, 1H, 2-H), 8.42 (d, 2H, J=7.91 Hz, 4", 5"-H), 8.49 (d, 2H, J=6.86 Hz, 2", 7"-H), 9.55 (s, 1H, 4'-OH). $^{13}$CNMR (DMSO-$d_6$) δ,38.1 (—N—$CH_2$—), 65.1 (—$CH_2$—O—), 101.0 (C-8), 114.95 (C-6), 115.0 (C-3', 5'), 117.7 (C-10), 121.9 (C-1", 8"), 122.3 (C-1'), 123.7 (C-3), 126.96 (C-9"), 127.2 (C-5), 127.4 (C-3", 6"), 130.1 (C-2', 6'), 130.9 (C-4",5"), 131.3 (C-10"), 134.5 (C-2", 7"), 153.1 (C-2), 157.2 (C-9), 157.3 (C-4'), 162.4 (C-7), 163.5 (N—C═O),174.6 (C-4). MS (m/z), 478.1 $(M+H)^+$, 516 $(M+K)^+$. Anal. ($C_{29}H_{19}O_6N$) for C, H, N. Cacld, 72.95, 4.01, 2.93, found, 71.35, 4.18, 2.85.

Daidzein 7-(2"-Carboxyfurfuryl) Ether (Analog 99)

The compound was prepared by hydrolysis of analog 89. To a solution of 1.0 g of analog 89 in 20 ml of methanol was added 2 ml of 2 N aq. KOH and 10 ml of water. The mixture was stirred and gently refluxed for 2 hours until all reactants were hydrolyzed (monitored by TLC). The reaction mixture was concentrated by flash evaporation and products were precipitated by adjusting the pH to 3-4. Precipitates were collected by filtration and purified by recrystallization from acetone to give 730 mg of crystalline analog 99. Analyses: yield, 73%. MS (m/z) 379.2 $(M+H)^+$, 401.2 $(M+Na)^+$, 417.3 $(M+K)^+$, 377.3 $(M-H)^-$. Elementary analyses ($C_{21}H_{14}O_7$) for C, H: Cacld 66.67, 3.73; found 65.78, 3.84.

EXAMPLE V

MAO and ALDH-2 Assays

Several of the synthesized compounds were tested for MAO and ALDH-2 suppression activity. The membrane and supernatant fractions of the lysate of a gradient purified hamster liver mitochondria preparation were used as sources of MAO and ALDH-2, respectively. ALDH-2 and MAO activity assays were performed according to established procedures (Rooke et al. (2000) *J. Med. Chem.* 43:4169).

EXAMPLE VI

Ethanol Drinking Experiments

Effects of the newly synthesized analogs on hamster ethanol intake were determined according to the method described below. Animals were male adult golden hamsters (outbred, Lakeview Lak: LVG[SYR]), purchased from Charles River Laboratories, Wilmington, Mass. 01887 or Harlan Sprague Dawley, Inc., Indianapolis, Ind. 46229. Upon arrival, hamsters were housed in a room maintained at 23° C., 35-45% humidity, with a 12/12 hr light/dark cycle (light on 0600-1800 hr), ad libitum access to Purina Chow (5001) and a 15% v/v ethanol solution. After a week, each hamster was transferred to an individual stainless steel cage (26×18×17.5 cm). Two 50 ml drinking bottles, one containing water and the other a 15% ethanol solution, were provided continuously. The bottles were placed in holders equipped with tilted platforms which direct spillage to tubes placed outside of the cages. The positions of the two drinking bottles on each cage were altered daily to prevent development of positional preference. Fluid intake was measured at 0900 hr each day. Hamsters that drank significant (>8 ml/day) and consistent (daily variance <±20%) amounts of ethanol solution were selected for testing. To establish baseline ethanol and water intake, 1 ml sterile saline was administered daily to each hamster between 1500-1600 hr for 6 days (saline control period, Day 1 to Day 6). A daily dose of 0.07 mmol of test compound was then administered for 5 consecutive days (treatment period, Day 7 to Day 11). After the last dose, ethanol and water intake were monitored for another 6 days (post treatment period, Day 12 to Day 17). The results demonstrated that these analogs, at a dose of 0.07 mmol/day/hamster, suppress hamster ethanol intake. Among the 17 active analogs tested, 5 of them (Analogs 81, 87, 88, 89, and 99) were more potent than daidzin. At an equivalent dose, daidzin suppressed ethanol intake by about 55% (Table 1).

TABLE 1

Ethanol Intake Suppressive Activity of Analogs of Daidzin

| Daidzin & Analog | EtOH intake suppression, % |
|---|---|
| 42 (Daidzin) | 55 ± 12 |
| 40 (Daidzein) | 22 ± 5 |
| Hexzein | 69 ± 12 |
| Hepzein | 69 ± 8 |
| Deczein | 84 ± 5 |
| Undeczein | 86 ± 7 |
| 50 | 46 ± 7 |
| 53 | 49 ± 8 |
| 57 | 57 ± 8 |
| 63 | 55 ± 10 |
| 6 | 54 ± 4 |

TABLE 1-continued

Ethanol Intake Suppressive Activity of Analogs of Daidzin

| Daidzin & Analog | EtOH intake suppression, % |
|---|---|
| 13 | 58 ± 5 |
| 73 | 44 ± 6 |
| 75 (half dose) | 36 ± 12 |
| 75 | 53 ± 4 |
| 14 | 37 ± 3 |
| 81 | 91 ± 2 |
| 83 | 44 ± 8 |
| 86 | 50 ± 4 |
| 87 | 73 ± 5 |
| 88 | 78 ± 9 |
| 89 | 83 ± 11 |
| 99 | 81 ± 9 |
| 26 | 32 ± 16 |
| 33 | 49 ± 7 |

EXAMPLE VII

Structure-Activity Relationship (SAR)

The effects of substitutions at the 2, 3', 4', 5, 6 and 8 positions of an isoflavone on the potencies for ALDH-2 and MAO inhibition were evaluated and results are set forth below.

Substitution of 4'-OH

Nine 4', 7-O-distributed analogs of daidzin were synthesized, and their ALDH-2 and MAO inhibitory activities were tested and compared with those of their respective 7-O-mono-substituted analogs. While all the mono-substituted analogs inhibited ALDH-2 ($IC_{50}$=0.08 to 9 μM), none of the di-substituted analogs were inhibitory (Gao et al. (2001) *J Med. Chem.* 44:3328). Among the mono-substituted analogs studied, three inhibited MAO and di-substitution abolished this activity as well. This indicated that either a free 4'-hydroxyl and/or a smaller 4'-substituent imparted antidipsotropic activity.

To further evaluate the SAR of 4'-substitution, two series of 7-O-substituted analogs were synthesized: the 7-O-substituted 4'-hydroxyisoflavones (analogs 2, 4, 6, 8, 11, and 13) and the 7-O-subtituted isoflavones (analogs 3, 5, 7, 9, 12, and 14). All members of the 7-O-substituted 4'-hydroxyisoflavone series were potent ALDH-2 inhibitors, with $IC_{50}$ values ranging from 0.04 μM to 0.28 μM. While the 7-O-substituted isoflavone derivatives also inhibited ALDH-2, they were less potent than their 4'-hydroxy counterparts, with $IC_{50}$ values ranging from 0.1 μM to 1.5 μM. In all cases, the 4'-OH/4'H substitutions decreased potencies for ALDH-2 inhibition, raising $IC_{50}$ values from 2-(analog 6 vs. analog 7) to 19-fold (analog 4 vs. analog 5). The effect of 4'-OH/4'H substitution on MAO inhibition, however, was more dramatic. While all members of the 4' hydroxyl derivatives (analogs 2, 4, 6, 8, 11 and 13) inhibited MAO, none of the 4'-H series (analogs 3, 5, 7, 9, 12 and 14) had any effect on MAO. The fact that the effect of 4'-OH/4'-H substitution was independent of the nature of the 7-O-substituents indicated that the 4'-hydroxyl can influence MAO inhibition.

While not intending to be bound by theory, replacing the 4'-OH with an H can serve to decrease the polarity and hydrogen bonding ability of an isoflavone molecule. Moreover, it can induce redistribution of electron density on the B-ring. These factors, alone or combined, can contribute to decreased ALDH-2 and/or MAO inhibition. To explore the effects of polarity, hydrogen bonding ability, and the electron donating and withdrawing property of the 4'-substituent on the potencies for MAO and ALDH-2 inhibition, two series of 4'-substituted analogs were synthesized and studied: the 7-O-ω-ethoxycarbonylpentyl- and the 7-hydroxyisoflavones. Among the 7-O-ω-ethoxycarbonylpentylisoflavones, the 4'-$NH_2$ (analog 33), 4'-OH (analog 6), and 4'-H (analog 7) were more potent ALDH-2 inhibitors than the 4'-F (analog 24), 4'-Br (analog 26), and 4'-$CH_3$ (analog 30) derivatives. The 4'-$NO_2$ derivative (analog 28) was not inhibitory. This indicated that polarity, hydrogen bonding ability and electron withdrawing and releasing properties of the 4'-substituent affect potency for ALDH-2 inhibition. The most potent inhibitors were those that had polar (low hydrophobic constants), electron releasing, and hydrogen bond forming 4'-substituents such as analog 33 (4'-$NH_2$) and analog 6 (4'-OH). The 4'-$CH_3$ (analog 30) and 4'-Br derivatives (analog 26) were highly lipophilic having $\pi$ values of 0.56 and 0.86 (Table 2), respectively, and were therefore, much less potent ALDH-2 inhibitors.

TABLE 2

Hydrophobic Constants of, and Changes in Chemical Shifts Induced by Various 4'-Substituted-7-O-ω-Ethoxycarbonylpentylisoflavones

| Analog | 4'-Substituent | $\pi^b$ | $^{13}$C-NMR[a] 1' | $^{13}$C-NMR[a] 2',6' | $^{13}$C-NMR[a] 3',5' | $^{13}$C-NMR[a] 4' |
|---|---|---|---|---|---|---|
| 4b | H | 0.00 | 0 (126.9) | 0 (128.9) | 0 (128.1) | 0 (131.9) |
| 2b[c] | H | 0.00 | 0.1 | −0.1 | 0 | −0.2 |
| 11b | F | 0.14 | 0 | 2.0 | −13.1 | 28.9 |
| 12b | Br | 0.86 | 0 | 2.0 | 2.9 | −0.7 |
| 13b | $NO_2$ | −0.28 | 12.2 | −5.7 | 1.8 | 14.9 |
| 14b | $CH_3$ | 0.56 | −3.3 | −0.2 | 0.6 | 5.2 |
| 4a | OH | −0.67 | −4.5 | 1.1 | −13.2 | 25.5 |
| 2a[c] | OH | −0.67 | −4.5 | 0.8 | −13.0 | 25.6 |
| 16b | $NH_2$ | −1.23 | −8.1 | 0.6 | −14.7 | 16.6 |

[a]4'-Substituents-induced chemical shifts, relative to those of analog 7. Actual δ values (ppm) for the analog 7 B-ring $^{13}$C signals are shown in parentheses.
[b]Hydrophobic constants, taken from Fujita et al. ((1964) J. Am. Chem. Soc. 86: 5175).
[c]Analogs 2 and analog 3 are 4'-substituted-7-O-methylisoflavones.

Despite the presence of the 1'-benzopyran function, electron density distributed rather evenly on the six carbons of the B-ring of analog 7 and analog 3 as indicated by the $^{13}$C-NMR data (Table 2). Substitution of 4'-H changed electron density distribution. Interestingly, 4'-substitutions that increased the electron densities at the C-1', C-3' and C5' (shifting the $^{13}$C-1', $^{13}$C-3' and $^{13}$C-5' signals up field) and decreased the electron densities at the C-4' (shifting the $^{13}$C-4' signal down field) had increased potencies for ALDH-2 inhibition (analog 2, analog 6, analog 24, analog 33), whereas those that only decreased electron density at the C-4' had decreased potencies for ALDH-2 inhibition (analog 28, analog 30).

All members of the 4'-substituted 7-hydroxyl derivatives inhibited MAO, with the 4'-$NO_2$ (analog 27) being most potent ($IC_{50}$=0.1 μm), followed by 4'-F (analog 23) (1.5 μm), 4'-Br (analog 25) (1.0 μm), 4'-H (1) (8.6 μm), 4'-$CH_3$ (analog 29) (9 μm), 4'-OH (analog 40) (12 μm), and 4'-$NH_2$-7-hydroxyisoflavone (analog 32) (12 μm). This indicated that potencies for MAO were linked positively to the electron withdrawing properties of the 4'-substituents: the analog that had the strongest electron withdrawing 4'-substituent ($NO_2$) also inhibited MAO most potently ($IC_{50}$=0.1 μM), whereas that with the strongest electron donating 4'-substituent ($NH_2$) was least inhibitory ($IC_{50}$>9 μm).

Substitution of 8-H

To evaluate the effect of C-8 substituents on ALDH-2 and MAO inhibition, two 8-C-glucosylated 7-O-substituted analogs were synthesized: 7-ethoxycarbonylpentoxy-puerarin (analog 36), 7-O-phthalimide-N-butylpuerarin (analog 17). One 8-methoxylated 7-O-substituted analog was synthesized: 7,8-dimethoxyisoflavone (analog 34). Their potencies for ALDH-2 and MAO inhibition were determined and compared with their 8-H substituted counterparts, 7-ethoxycarbonyl-pentoxydaidzein (analog 6), 2-carboxy-7-O-phthalimide-N-butyldaidzein (analog 13), and 7-methoxyisoflavone (analog 3), respectively. Results indicated that replacing the 8-H with either a glucosyl (analog 36 and analog 17) or a methoxy function (analog 34) (i) completely abolished ALDH-2 inhibitory activities, and (ii) substantially decreased potencies for MAO inhibition.

Substitutions at 5, 2, 6, and 3' Positions

The 5-hydroxyl substituted 7-methoxydaidzein (analog 2 vs. analog 45) had decreased potency for ALDH-2 inhibition. This, together with the finding that hydroxyl substitution at the 5 position increased potency for MAO inhibition (analog 40 vs. analog 43, analog 2 vs. analog 45, analog 41 vs. analog 46), indicated that a 5-OH function can contribute negatively to antidipsotropic activity.

One 2-methyl derivative (analog 39), one 2-carboxy derivative (analog 16), and two 2-ethoxycarbonyl derivatives (analog 15, analog 19) were prepared, and their potencies for ALDH-2 inhibition were determined and compared with their respective non-substituted counterparts, analogs analog 10, analog 14, and analog 18. While analog 10, analog 14, and analog 18 inhibited ALDH-2 fairly potently, with $IC_{50}$ values ranging from 8 μM to 0.14 μM, none of their 2-substituted derivatives exhibited inhibitory activity toward ALDH-2. Three additional 2-substituted analogs, analog 20, analog 21 and analog 22, were also tested and shown to have no effect on ALDH-2 activity. Without wishing to be bound by theory, these results indicated that the 2 position of daidzin or its active analogs occupies an important area on the enzyme binding site.

A series of daidzin analogs having 4'-OR groups replaced with H (analogs 3, 5, 7, 9, 10, 12, 14, and 19), F (analog 23, 24), Br (analog 25, 26), $CH_3$ (analog 29,30), $NH_2$ (analog 32, 33), $NO_2$ (analog 27, 28), or $OCH_3$ (analog 41) substituents were prepared. Their potencies for ALDH-2 and MAO inhibition were determined and compared among each other and with those of their respective 7-O-substituted derivatives of daidzein. Results revealed that the potency for ALDH-2 inhibition of a daidzin analog was associated with a polar 4'-substituent with electron donating and hydrogen bonding ability such as —$NH_2$ and —OH, whereas that for MAO inhibition was positively linked to the electron withdrawing property of the 4'-substituent. In ALDH-2, the 2, 3', 5, 6 and 8 positions of a bound inhibitor were located in relatively restricted areas and attempts to replace the —H atom on any of these positions resulted in complete loss of ALDH-2 inhibitory activity. Thus, a potent antidipsotropic analog of daidzin is a 4', 7-disubstituted isoflavone. In one embodiment, a 4'-substituent is small, polar, can release one or more electrons, and/or can bind hydrogen. In another embodiment, a 4'-substituent is —OH or $NH_2$. In yet another embodiment, a 7-substituent is a straight-chain alkyl optionally having a terminal polar function. In yet another embodiment, a 7-substituent is $-(CH_2)_n-OH$, $(CH_2)_n-COOH$ or $-(CH_2)_n-NH_2$, wherein $2 \leqq n \leqq 6$, $5 \leqq n \leqq 10$, $n \geqq 4$, respectively.

In one embodiment, an antidipsotropic compound does not inhibit MAO activity. In another embodiment, an antidipsotropic compound partially inhibits MAO activity. As used herein, the term "partially inhibits" refers to an inhibition of 75%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1% or less of the wild-type activity.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application were specifically and individually indicated to be so incorporated by reference.

What is claimed is:

1. A method of reducing alcohol consumption in a mammal comprising administering a compound of Formula I Formula I

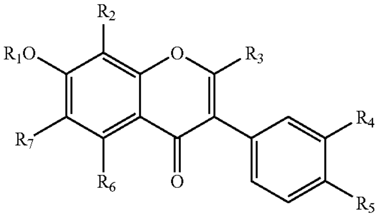

wherein:

$R_1$ is selected from the group consisting of hydrogen, carboxy, halo, branched or straight chain ($C_1$-$C_6$)haloalkyl, ($C_3$-$C_6$)cycloalkoxy, ($C_1$-$C_6$)haloalkoxy, ($C_3$-$C_6$)cyclohaloalkoxy, ($C_3$-$C_6$)cycloalkoxyalkyl, ($C_1$-$C_6$)alkoxy($C_3$-$C_6$)cycloalkyl, ($C_3$-$C_6$)cycloalkylcarbonyl, substituted or unsubstituted phenyl, phenyl($C_1$-$C_6$)alkyl, and heterocyclyloxy, heterocyclylcarbonyl, wherein substituents are from one to four and are selected from the group consisting of halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, and di($C_1$-$C_3$)alkylaminocarbonyl;

$R_2$ is selected from the group consisting of hydrogen and alkoxy;

$R_3$ is selected from the group consisting of hydrogen, ($C_1$-$C_6$) alkoxycarbonyl, and carboxy;

$R_4$ is selected from the group consisting of hydrogen and hydroxy;

$R_5$ is selected from the group consisting of hydrogen, carboxy, hydroxy, amino, halo, branched or straight chain ($C_1$-$C_6$)alkyl, ($C_1$-$C_6$)haloalkyl, ($C_2$-$C_6$)alkenyl, ($C_3$-$C_6$)alkadienyl, ($C_1$-$C_6$)alkoxy, ($C_3$-$C_6$)cycloalkoxy, ($C_1$-$C_6$)haloalkoxy, ($C_3$-$C_6$)cyclohaloalkoxy, ($C_2$-$C_6$)alkynyloxy, ($C_1$-$C_6$)alkoxy($C_1$-$C_6$)alkyl, ($C_3$-$C_6$)cycloalkoxyalkyl, $C_1$-$C_6$)alkoxy($C_3$-$C_6$)cycloalkyl, ($C_1$-$C_6$)alkylcarbonyl, ($C_3$-$C_6$)cycloalkylcarbonyl, ($C_1$-$C_6$)alkoxycarbonyl, ($C_4$-$C_6$)alkoxycarbonylalkyl, ($C_1$-$C_6$)hydroxyalkyl, substituted or unsubstituted phenyl, phenyl($C_1$-$C_6$)alkyl, heterocyclyl, heterocyclyloxy, heterocyclylcarbonyl, wherein substituents are from one to four and are selected from the group consisting of halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkylamino, di($C_1$-$C_3$)alkylamino, ($C_1$-$C_2$)alkoxy($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, and di($C_1$-$C_3$)alkylaminocarbonyl;

$R_6$ is selected from the group consisting of hydrogen and hydroxy; and $R_7$ is selected from the group consisting of hydrogen and halogen, with the proviso that $R_5$ cannot be hydroxy when $R_1$, $R_2$, $R_3$, $R_4$, $R_6$, and $R_7$ are all hydrogen in an amount effective to increase a concentration of 5-hydroxyindoleacetaldehyde formed during catabolism of serotonin or dopamine.

2. A method of modulating alcohol consumption in mammal comprising administering a compound of Formula I Formula I

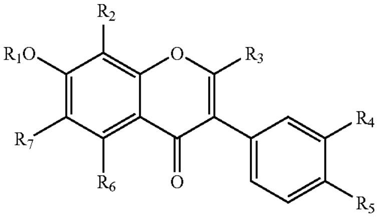

wherein:

$R_1$ is selected from the group consisting of hydrogen, carboxy, halo, branched or straight ($C_1$-$C_6$)alkyl, ($C_1$-$C_6$)haloalkyl, ($C_2$-$C_6$)alkenyl, ($C_3$-$C_6$)alkadienyl, ($C_1$-$C_6$)alkoxy, ($C_3$-$C_6$)cycloalkoxy, ($C_1$-$C_6$)haloalkoxy, ($C_3$-$C_6$)cyclohaloalkoxy, ($C_2$-$C_6$)alkynyloxy, ($C_1$-$C_6$)alkoxy($C_1$-$C_6$)alkyl, ($C_3$-$C_6$)cycloalkoxyalkyl, ($C_1$-$C_6$)alkoxy($C_3$-$C_6$)cycloalkyl, ($C_1$-$C_6$)alkylcarbonyl, ($C_3$-$C_6$)cycloalkylcarbonyl, ($C_1$-$C_6$)alkoxycarbonyl, ($C_4$-$C_6$)alkoxycarbonylalkyl, ($C_1$-$C_6$)hydroxyalkyl, ($C_5$-$C_{10}$)carboxyalkyl, substituted or unsubstituted phenyl, phenyl($C_1$-$C_6$)alkyl, heterocyclyl, heterocyclyloxy, heterocyclylcarbonyl, wherein substituents are from one to four and are selected from the group consisting of halo, aminocarbonyl, aminothiocarbonyl, carboxy, formyl, hydroxy, amino, carbamoyl, ($C_1$-$C_3$)alkyl, ($C_1$-$C_3$)haloalkyl, ($C_1$-$C_3$)alkoxy, ($C_1$-$C_3$)haloalkoxy, ($C_1$-$C_3$)alkylamino, di($C_1$-$C_3$)alkylamino, ($C_1$-$C_2$)alkoxy ($C_1$-$C_2$)alkyl, ($C_1$-$C_2$)alkylamino($C_1$-$C_2$)alkyl, di($C_1$-$C_2$)alkylamino($C_1$-$C_2$)alkyl, ($C_1$-$C_3$)alkylcarbonyl, ($C_1$-$C_3$)alkoxycarbonyl, ($C_1$-$C_3$)alkylaminocarbonyl, and di($C_1$-$C_3$)alkylaminocarbonyl;

$R_2$ is selected from the group consisting of hydrogen and alkoxy;

$R_3$ is selected from the group consisting of hydrogen ($C_1$-$C_6$)alkoxycarbonyl, and carboxy;

$R_4$ is selected from the group consisting of hydrogen and hydroxy;

$R_5$ is selected from the group consisting of hydrogen, carboxy, halo, amino, branched or straight chain $(C_1$-$C_6)$alkyl, $(C_1$-$C_6)$haloalkyl, $(C_2$-$C_6)$alkenyl, $(C_3$-$C_6)$ alkadienyl, $(C_1$-$C_6)$alkoxy, $(C_3$-$C_6)$cycloalkoxy, $(C_1$-$C_6)$haloalkoxy, $(C_3$-$C_6)$cyclohaloalkoxy, $(C_2$-$C_6)$ alkynyloxy, $(C_1$-$C_6)$alkoxy$(C_1$-$C_6)$alkyl, $(C_3$-$C_6)$ cycloalkoxyalkyl, $(C_1$-$C_6)$alkoxy$(C_3$-$C_6)$cycloalkyl, $(C_1$-$C_6)$alkylcarbonyl, $(C_3$-$C_6)$cycloalkylcarbonyl, $(C_1$-$C_6)$alkoxycarbonyl, $(C_4$-$C_6)$alkoxycarbonylalkyl, $(C_1$-$C_6)$hydroxyalkyl, substituted or unsubstituted phenyl, phenyl$(C_1$-$C_6)$alkyl, heterocyclyl, heterocyclyloxy, heterocyclylcarbonyl, wherein substituents are from one to four and are selected from the group consisting of halo, aminocarbonyl, aminothiocarbonyl, carboxy, formyl, hydroxy, amino, carbamoyl, $(C_1$-$C_3)$ alkyl, $(C_1$-$C_3)$haloalkyl, $(C_1$-$C_3)$alkoxy, $(C_1$-$C_3)$haloalkoxy, $(C_1$-$C_3)$alkylamino, di$(C_1$-$C_3)$alkylamino, $(C_1$-$C_2)$alkoxy$(C_1$-$C_2)$alkyl, $(C_1$-$C_2)$alkylamino$(C_1$-$C_2)$alkyl, di$(C_1$-$C_2)$alkylamino$(C_1$-$C_2)$alkyl, $(C_1$-$C_3)$ alkylcarbonyl, $(C_1$-$C_3)$alkoxycarbonyl, $(C_1$-$C_3)$alkylaminocarbonyl, and di$(C_1$-$C_3)$alkylaminocarbonyl;

$R_6$ is selected from the group consisting of hydrogen and hydroxy; and $R_7$ is selected from the group consisting of hydrogen, halogen, and $C_1$-$C_6$ alkoxy, in an amount effective to increase a concentration of 5-hydroxyindoleacetaldehyde or 3,4-dihydroxyphenylacetaldehyde formed during catabolism of serotonin or dopamine.

3. The method of claim 1, wherein the mammal is a human.

4. The method of claim 1, wherein the compound does not inhibit monoamine oxidase.

5. The method of claim 1, wherein $R_5$ is hydroxyl or amino.

6. The method of claim 2, wherein $R_1$ is a straight chain alkyl.

7. The method of claim 2, wherein $R_1$ is $(C_1C_6)$hydroxyalkyl or $(C_5C_{10})$carboxyalkyl.

8. The method of claim 1, wherein the compound is administered intraperitoneally, intramuscularly or orally.

9. A compound for inhibiting ALDH-2 comprising Formula I

Formula I

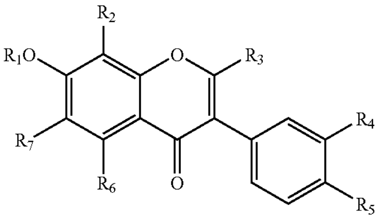

wherein:

$R_1$ is selected from the group consisting of hydrogen, carboxy, halo, amino, branched or straight chain $(C_1$-$C_6)$alkyl, $(C_1$-$C_6)$haloalkyl, $(C_2$-$C_6)$alkenyl, $(C_3$-$C_6)$ alkadienyl, $(C_1$-$C_6)$alkoxy, $(C_3$-$C_6)$cycloalkoxy, $(C_1$-$C_6)$haloalkoxy, $(C_3$-$C_6)$cyclohaloalkoxy, $(C_2$-$C_6)$ alkynyloxy, $(C_1$-$C_6)$alkoxy$(C_1$-$C_6)$alkyl, $(C_3$-$C_6)$ cycloalkoxyalkyl, $(C_1$-$C_6)$alkoxy$(C_3$-$C_6)$cycloalkyl, $(C_1$-$C_6)$alkylcarbonyl, $(C_3$-$C_6)$cycloalkylcarbonyl, $(C_1$-$C_6)$alkoxycarbonyl, $(C_4$-$C_6)$alkoxycarbonylalkyl, $(C_1$-$C_6)$hydroxyalkyl, $(C_5$-$C_{10})$carboxyalkyl, substituted or unsubstituted phenyl, phenyl$(C_1$-$C_6)$alkyl, heterocyclyl, heterocyclyloxy, heterocyclylcarbonyl, wherein substituents are from one to four and are selected from the group consisting of halo, aminocarbonyl, aminothiocarbonyl, carboxy, formyl, hydroxy, amino, carbamoyl, $(C_1$-$C_3)$alkyl, $(C_1$-$C_3)$haloalkyl, $(C_1$-$C_3)$alkoxy, $(C_1$-$C_3)$haloalkoxy, $(C_{1\text{-}C3})$alkylamino, di$(C_1$-$C_3)$alkylamino, $(C_1$-$C_2)$alkoxy$(C_1$-$C_2)$alkyl, $(C_1$-$C_2)$alkylamino$(C_1$-$C_2)$alkyl, di$(C_1$-$C_2)$alkylamino$(C_1$-$C_2)$alkyl, $(C_1$-$C_3)$alkylcarbonyl, $(C_1$-$C_3)$alkoxycarbonyl, $(C_1C_3)$alkylaminocarbonyl, and di$(C_1$-$C_3)$ alkylaminocarbonyl;

$R_2$ is selected from the group consisting of hydrogen and alkoxy;

$R_3$ is hydrogen;

$R_4$ is selected from the group consisting of hydrogen and hydroxy;

$R_5$ is selected from the group consisting of hydrogen, carboxy, halo, amino, branched or straight chain $(C_1$-$C_6)$alkyl, $(C_1$-$C_6)$haloalkyl, $(C_2$-$C_6)$alkenyl, $(C_3$-$C_6)$ alkadienyl, $(C_1$-$C_6)$alkoxy, $(C_3$-$C_6)$cycloalkoxy, $(C_1$-$C_6)$haloalkoxy, $(C_3$-$C_6)$cyclohaloalkoxy, $(C_2$-$C_6)$ alkynyloxy, $(C_1$-$C_6)$alkoxy$(C_1$-$C_6)$alkyl, $(C_3$-$C_6)$ cycloalkoxyalkyl, $(C_1$-$C_6)$alkoxy$(C_3$-$C_6)$cycloalkyl, $(C_1$-$C_6)$alkylcarbonyl, $(C_3$-$C_6)$cycloalkylcarbonyl, $(C_1$-$C_6)$alkoxycarbonyl, $(C_4$-$C_6)$alkoxycarbonylalkyl, $(C_1$-$C_6)$hydroxyalkyl, substituted or unsubstituted phenyl, phenyl$(C_1$-$C_6)$alkyl, heterocyclyl, heterocyclyloxy, heterocyclylcarbonyl, wherein substituents are from one to four and are selected from the group consisting of halo, aminocarbonyl, aminothiocarbonyl, carboxy, formyl, hydroxy, amino, carbamoyl, $(C_1$-$C_3)$ alkyl, $(C_1$-$C_3)$haloalkyl, $(C_1$-$C_3)$alkoxy, $(C_1$-$C_3)$haloalkoxy, $(C_1$-$C_3)$alkylamino, di$(C_1$-$C_3)$alkylamino, $(C_1$-$C_2)$alkoxy$(C_1$-$C_2)$alkyl, $(C_1$-$C_2)$alkylamino$(C_1$-$C_2)$alkyl, di$(C_1$-$C_2)$alkylamino$(C_1$-$C_2)$alkyl, $(C_1$-$C_3)$ alkylcarbonyl, $(C_1$-$C_3)$alkoxycarbonyl, $(C_1$-$C_3)$alkylaminocarbonyl, and di$(C_1$-$C_3)$alkylaminocarbonyl;

$R_6$ is selected from the group consisting of hydrogen and hydroxy; and $R_7$ is selected from the group consisting of hydrogen, halogen, and $C_1$-$C_6$ alkoxy.

10. The compound of claim 9, wherein $R_5$ is hydroxyl or amino.

11. The compound of claim 9, wherein $R_1$ is a straight chain alkyl.

12. The compound of claim 9, wherein $R_1$ is $(C_1$-$C_6)$ hydroxyalkyl or $(C_5$-$C_{10})$carboxyalkyl.

* * * * *